(12) United States Patent
Wang et al.

(10) Patent No.: US 9,340,523 B2
(45) Date of Patent: *May 17, 2016

(54) CERTAIN DIPEPTIDYL PEPTIDASE INHIBITORS

(71) Applicant: FOCHON PHARMA, INC., San Leandro, CA (US)

(72) Inventors: Weibo Wang, Moraga, CA (US); Tongshuang Li, Surrey (CA)

(73) Assignee: FOCHON PHARMA, INC., San Leandro, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/146,749

(22) Filed: Jan. 3, 2014

(65) Prior Publication Data

US 2014/0213590 A1 Jul. 31, 2014

Related U.S. Application Data

(63) Continuation of application No. 12/979,571, filed on Dec. 28, 2010, now Pat. No. 8,648,073.

(60) Provisional application No. 61/291,321, filed on Dec. 30, 2009.

(51) Int. Cl.
*A61K 31/53* (2006.01)
*C07D 401/04* (2006.01)

(52) U.S. Cl.
CPC .................... *C07D 401/04* (2013.01)

(58) Field of Classification Search
CPC ............................ C07D 401/04; A61K 31/53
USPC .......................................... 514/242; 544/182
See application file for complete search history.

(56) References Cited

U.S. PATENT DOCUMENTS

| | | | |
|---|---|---|---|
| 3,710,795 A | 1/1973 | Higuchi et al. | |
| 4,044,126 A | 8/1977 | Cook et al. | |
| 4,166,452 A | 9/1979 | Generales, Jr. | |
| 4,256,108 A | 3/1981 | Theeuwes | |
| 4,265,874 A | 5/1981 | Bonsen et al. | |
| 4,328,245 A | 5/1982 | Yu et al. | |
| 4,364,923 A | 12/1982 | Cook et al. | |
| 4,409,239 A | 10/1983 | Yu | |
| 4,410,545 A | 10/1983 | Yu et al. | |
| 4,414,209 A | 11/1983 | Cook et al. | |
| 5,292,736 A | 3/1994 | Kumar et al. | |
| 5,532,237 A | 7/1996 | Gallant et al. | |
| 5,624,941 A | 4/1997 | Barth et al. | |
| 6,028,084 A | 2/2000 | Barth et al. | |
| 6,335,345 B1 | 1/2002 | Fukami et al. | |
| 6,706,742 B2 | 3/2004 | De Nanteuil et al. | |
| 7,169,926 B1 | 1/2007 | Burgess et al. | |
| 8,648,073 B2 * | 2/2014 | Wang et al. ................. | 514/242 |

FOREIGN PATENT DOCUMENTS

| | | |
|---|---|---|
| EP | 1 258 476 A1 | 11/2002 |
| WO | WO 97/28149 A1 | 8/1997 |
| WO | WO 98/04528 A2 | 2/1998 |
| WO | WO 98/41519 A1 | 9/1998 |
| WO | WO 99/01423 A1 | 1/1999 |
| WO | WO 99/02499 A1 | 1/1999 |
| WO | WO 99/56753 A1 | 11/1999 |
| WO | WO 99/64002 A1 | 12/1999 |
| WO | WO 00/10968 A2 | 3/2000 |
| WO | WO 00/39088 A1 | 7/2000 |
| WO | WO 00/42026 A1 | 7/2000 |
| WO | WO 00/56297 A2 | 9/2000 |
| WO | WO 00/58360 A2 | 10/2000 |
| WO | WO 00/59887 A1 | 10/2000 |
| WO | WO 00/69810 A1 | 11/2000 |
| WO | WO 00/74679 A1 | 12/2000 |
| WO | WO 01/14376 A1 | 3/2001 |
| WO | WO 01/23420 A2 | 4/2001 |
| WO | WO 01/70337 A1 | 9/2001 |
| WO | WO 01/70708 A1 | 9/2001 |
| WO | WO 02/34243 A2 | 5/2002 |
| WO | WO 02/062764 A1 | 8/2002 |
| WO | WO 02/068388 A2 | 9/2002 |
| WO | WO 02/076949 A1 | 10/2002 |
| WO | WO 02/083128 A1 | 10/2002 |
| WO | WO 03/000180 A2 | 1/2003 |
| WO | WO 03/000181 A2 | 1/2003 |
| WO | WO 03/000250 A1 | 1/2003 |
| WO | WO 03/002530 A2 | 1/2003 |
| WO | WO 03/002531 A2 | 1/2003 |
| WO | WO 03/002553 A2 | 1/2003 |
| WO | WO 03/002593 A2 | 1/2003 |
| WO | WO 03/004496 A1 | 1/2003 |

(Continued)

OTHER PUBLICATIONS

Bongers, J. et al., "Kinetics of Dipeptidyl Peptidase IV Proteolysis of Growth Hormone-Releasing Factor and Analogs," Biochimica et Biophysica Acta, 1122(2), pp. 147-153 (1992), Elsevier Science Publishers, B.V.
Chaki, S. et al., "Recent Advance in Feeding Suppressing Agents: Potential Therapeutic Strategy for the Treatment of Obesity," Expert Opin. Ther. Patents, 11(11), pp. 1677-1692 (2001), Ashley Publications Ltd.
Cox, S.W. et al., "Dipeptidyl Peptidase II- and IV-Like Activities in Gingival Tissue and Crevicular Fluid From Human Periodontitis Lesions," Archs Oral Biol., 37(3), pp. 167-173 (1992), Pergamon Press plc., Great Britain.
De Meester, I. et al., "CD26, Let It Cut or Cut It Down," Immunology Today, 20(8), pp. 367-375 (1999), Elsevier Science Ltd.
During, M.J. et al., "Glucagon-Like Peptide-1 Receptor is Involved in Learning and Neuroprotection," Nature Medicine 9(9), pp. 1173-1179 (2003), Nature Publishing Group.
Frohman, L. A. et al., "Dipeptidylpeptidase IV and Trypsin-Like Enzymatic Degradation of Human Growth Hormone-Releasing Hormone in Plasma," J. Clin. Invest. 83, pp. 1533-1540 (1989), The American Society for Clinical Investigation, Inc.

(Continued)

*Primary Examiner* — James O Wilson
*Assistant Examiner* — Ebenezer O Sackey
(74) *Attorney, Agent, or Firm* — Finnegan, Henderson, Farabow, Garrett & Dunner LLP

(57) ABSTRACT

Provided are certain dipeptidyl peptidase inhibitors, pharmaceutical compositions thereof, and methods of use therefor.

14 Claims, No Drawings

(56) References Cited

FOREIGN PATENT DOCUMENTS

| WO | WO 03/004498 A1 | 1/2003 |
|---|---|---|
| WO | WO 03/007887 A2 | 1/2003 |
| WO | WO 03/009847 A1 | 2/2003 |
| WO | WO 03/011262 A2 | 2/2003 |
| WO | WO 2004/087053 A2 | 10/2004 |
| WO | WO 2004/103993 A1 | 12/2004 |
| WO | WO 2005/016911 A1 | 2/2005 |
| WO | WO 2005/026148 A1 | 3/2005 |
| WO | WO 2005/030751 A2 | 4/2005 |
| WO | WO 2005/095381 A1 | 10/2005 |
| WO | WO 2005/118555 A1 | 12/2005 |
| WO | WO 2006/068978 A2 | 6/2006 |
| WO | WO 2006/090915 A1 | 8/2006 |
| WO | WO 2007/033350 A1 | 3/2007 |
| WO | WO 2007/035629 A2 | 3/2007 |
| WO | WO 2007/074884 A1 | 7/2007 |
| WO | WO 2007/112347 A1 | 10/2007 |
| WO | WO 2007/112368 A1 | 10/2007 |
| WO | WO 2008/033851 A2 | 3/2008 |
| WO | WO 2008/067465 A1 | 6/2008 |
| WO | WO 2008/114800 A2 | 9/2008 |
| WO | WO 2010/006962 A1 | 1/2010 |

OTHER PUBLICATIONS

Grimsby, J. et al., "Allosteric Activators of Glucokinase: Potential Role in Diabetes Therapy," Science, 301, pp. 370-373 (2003), American Association for the Advancement of Science, Washington, DC.

Iwata, S. et al., "CD26/Dipeptidyl Peptidase IV in Context: the Different Roles of a Multifunctional Ectoenzyme in Malignant Transformation," J. Exp. Med., 190(3), pp. 301-305 (1999), The Rockefeller University Press.

Karl, T. et al., "Extreme Reduction of Dipeptidyl Peptidase IV Activity in F344 Rat Substrains is Associated With Various Behavioral Differences," Physiology & Behavior, 80, pp. 123-134 (2003), Elsevier Inc.

Korom, S. et al., "Inhibition of CD26/Dipeptidyl Peptidase IV Activity in vivo Prolongs Cardiac Allograft Survival in Rat Recipients," Transplantation, 63(10), pp. 1495-1500 (1997), Williams & Wilkins, USA.

Lovshin, J. et al., "New Frontiers in the Biology of GLP-2," Regulatory Peptides, 90, pp. 27-32 (2000), Elsevier Science B.V.

Näslund, E. et al., "GLP-1 Slows Solid Gastric Emptying and Inhibits Insulin, Glucagon, and PYY Release in Humans," Am. J. Physiol. Regl. Integr. Comp. Physiol., 277, pp. 910-916 (1999), the American Physiological Society.

Scrocchi, L.A. et al., "Glucose Intolerance but Normal Satiety in Mice With a Null Mutation in the Glucago-Like Peptide 1 Receptor Gene," Nature Medicine, 2(11), pp. 1254-1258 (1996), Nature Publishing Group.

Shane, R. et al., "Modulation of Endomorphin-2-Induced Analgesia by Dipeptidyl Peptidase IV," Brain Research, 815, pp. 278-286 (1999), Elsevier Science B.V.

Shioda, T. et al., "Anti-HIV-1 and Chemotactic Activities of Human Stromal Cell-Derived Factor 1α (SDF-1 α) and SDF-1β are Abolished by CD26/Dipeptidyl Peptidase IV-Mediated Cleavage," Proc. Natl. Acad. Sci., 95, pp. 6331-6336 (1998), the National Academy of Sciences.

Spanswick, D. et al., "Emerging Antiobesity Drugs," Expert Opin. Emerging Drugs, 8(1), pp. 217-237 (2001), Ashley Publications Ltd.

Speake, J.D. et al., "Recent Advances in the Development of Melanocortin-4 Receptor Agonist," Expert Opin. Ther. Patents, 12(11), pp. 1631-1638 (2002), Ashley Publications Ltd.

Tanaka, S. et al., "Anti-Arthritic Effects of the Novel Dipeptidyl Peptidase IV Inhibitors TMC-2A and TSL-225," Immunopharmacology, 40, pp. 21-26 (1998), Elsevier Science B.V.

Tanaka, S. et al., "Suppression of Arthritis by the Inhibitors of Dipeptidyl Peptidase IV," Int. J. Immunopharmac., 19(1), pp. 15-24 (1997), Elsevier Science LTD, Great Britain.

Tang-Christensen, M. et al., "The Proglucagon-Derived Peptide, Glucagon-Like Peptide-2, is a Neurotransmitter Involved in the Regulation of Food Intake," Nature Medicine, 6(7), pp. 802-807 (2000), Nature Publishing Group.

Vanhoof, G. et al., "Distribution of Proline-Specific Aminopeptidases in Human Tissues and Body Fluids," Eur. J. Clin. Chem. Clin. Biochem., 30(6), pp. 333-338 (1992), Walter De Gruyter & Co. Berlin—New York.

Wu, Y. et al., "Neuroprotective Effects of Inhibitors of Dipeptidyl Peptidase-IV in vitro and in vivo" Int. Conf.on Dipeptidyl Aminopeptidases: Basic Science and Clinical Applications, Sep. 26-29, 2002 (Berlin,Germany).

\* cited by examiner

CERTAIN DIPEPTIDYL PEPTIDASE INHIBITORS

This is a continuation of application Ser. No. 12/979,571, filed on Dec. 28, 2010, now U.S. Pat. No. 8,648,073, issued Feb. 11, 2014, which claims priority of U.S. Provisional Application No. 61/291,321, filed on Dec. 30, 2009. The contents of both applications are incorporated herein by reference.

Provided are certain compounds and/or pharmaceutically acceptable salts thereof which can inhibit dipeptidyl peptidase IV (DPP-IV) and may be useful for the treatment of diabetes, such as type II diabetes, as well as hyperglycemia, metabolic syndrome, hyperinsulinemia, obesity, cardiovascular diseases and disorders such as atherosclerosis, cerebrovascular diseases, diseases and disorders of the central nervous system including schizophrenia, anxiety, bipolar disease, depression, insomnia, cognitive disorders, gastrointestinal diseases and disorders, cancer, inflammation and inflammatory diseases, respiratory diseases and disorders, musculoskeletal disorders, osteoporosis, menopausal symptoms and disorders, periodontal diseases such as gingivitis, and various immunomodulatory diseases.

Dipeptidyl peptidase IV (DPP-IV, CD26, EC 3.4.14.5) is a serine protease with specificity for cleaving Xaa-Pro and, to a lesser extent, Xaa-Ala dipeptides from the N-termini of polypeptides and proteins. DPP-IV is a non-classical serine protease in that the catalytic triad of Ser-Asp-His, found in the C-terminal region of the enzyme, is in reverse order to that found in classical serine proteases. DPP-IV is widely expressed in mammalian tissue as a type II integral membrane protein. DPP-IV is expressed on the surface of differentiated epithelial cells of the intestine, liver, kidney proximal tubules, prostate, corpus luteum, and on leukocyte subsets such as lymphocytes and macrophages. A soluble form of the enzyme is found in serum that has structure and function identical to the membrane-bound form of the enzyme but lacks the hydrophobic trans-membrane domain.

DPP-IV has many physiologically relevant substrates such as chemokines, RANTES (regulated on activation normal T-cell expressed and secreted), eotaxin, and macrophage-derived chemokine, neuropeptides such as NPY (neuropeptide Y) and substance $P_5$ vasoactive peptides, and incretins such as GLP-1 (glucagon-like peptide-1) and GIP (gastric inhibitory peptide/glucose-dependent insulinotropic polypeptide).

GLP-1 (7-36) is a 29 amino-acid peptide derived by post-translational processing of proglucagon in the small intestine. GLP-1 (7-36) may have multiple actions in vivo, for example, the stimulation of insulin secretion, inhibition of glucagon secretion, the promotion of satiety, and the slowing of gastric emptying. Based on its physiological profile, the actions of GLP-1 (7-36) are believed to be beneficial in the treatment of type II diabetes and potentially obesity. For example, exogenous administration of GLP-1 (7-36) (continuous infusion) in diabetic patients has been found to be efficacious in this patient population. Unfortunately, GLP-1 (7-36) can be degraded rapidly in vivo and has been shown to have a short half-life in vivo ($t_{1/2}$=1.5 minutes).

Based on a study of genetically bred DPP-IV knockout mice and on in vivo/in vitro studies with selective DPP-IV inhibitors, DPP-IV has been shown to be the primary degrading enzyme of GLP-1 (7-36) in vivo. GLP-1 (7-36) can be degraded by DPP-IV efficiently to GLP-1 (9-36), which has been speculated to act as a physiological antagonist to GLP-1 (7-36). Inhibiting DPP-IV in vivo is therefore believed to be useful for potentiating endogenous levels of GLP-1 (7-36) and attenuating the formation of its antagonist GLP-1 (9-36). Thus, DPP-IV inhibitors are believed to be useful agents for the treatment of conditions mediated by DPP-IV, such as diabetes and further such as, type II diabetes mellitus, diabetic dislipidemia, conditions of impaired glucose tolerance (IGT), conditions of impaired fasting plasma glucose (IFG), metabolic acidosis, ketosis, appetite regulation and obesity.

The inhibition of DPP-IV can provide for an attractive therapeutic treatment for type II diabetes and obesity. Although DPP-IV inhibitors may have demonstrated improved glucose tolerance in type II diabetes, many suffer from having short half-life and toxicity. Therefore, there is a need for new DPP-IV inhibitors that have at least one advantageous property selected from potency, stability, selectivity, toxicity and pharmacodynamics properties as an alternative for the treatment of type II diabetes. In this regard, a novel class of DPP-IV inhibitors is provided herein.

Provided is at least one compound of formula (I):

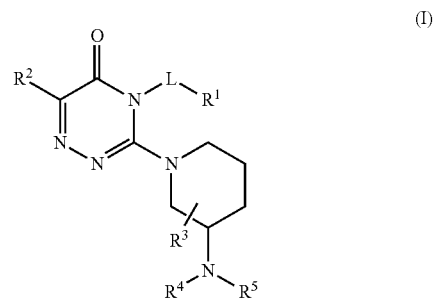

and/or at least one pharmaceutically acceptable salt thereof, wherein $R^1$ is selected from:
  $C_{1-10}$ alkyl,
  $C_{3-10}$ cycloalkyl,
  $C_{3-10}$ cycloalkyl-alkyl,
  heterocyclyl,
  heterocyclylalkyl
  aryl,
  arylalkyl,
  heteroaryl, and
  heteroarylalkyl,
    wherein alkyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or independently substituted with at least one substituent, such as one, two, three, or four substituents, independently selected from $R^{6b}$;

$R^2$ is selected from:
  hydrogen and
  alkyl,
    wherein each alkyl is unsubstituted or substituted with at least one substituent, such as one, two, three, or four substituents, independently selected from $R^{6a}$;

$R^3$ is selected from:
  hydrogen,
  halogen,
  hydroxyl,
  $C_{1-4}$ alkyl,
  $C_{2-4}$ alkenyl,
  $C_{2-4}$ alkynyl,
  $C_{3-7}$ cycloalkyl, heterocyclyl,
C$_{3-7}$ cycloalkylalkyl,
heterocyclylalkyl,
aryl,
heteroaryl,
arylalkyl, and
heteroarylalkyl,
wherein alkyl, alkenyl, alkynyl, cycloalkyl, and heterocyclyl are each unsubstituted or substituted with at least one substituent, such as one, two, three, or four substituents, independently selected from R$^{6a}$, and each aryl and heteroaryl is unsubstituted or substituted with at least one substituent, such as one, two, three, or four substituents, independently selected from R$^{6b}$;

R$^4$ is selected from:
hydrogen, and
C$_{1-4}$ alkyl,
wherein alkyl is unsubstituted or substituted with at least one substituent, such as one, two, three, or four substituents, independently selected from R$^{6a}$;

R$^5$ is selected from:
hydrogen, and
C$_{1-4}$ alkyl,
wherein alkyl is unsubstituted or substituted with at least one substituent, such as one, two, three, or four substituents, independently selected from R$^{6a}$;

or R$^4$ and R$^5$ together with the nitrogen to which they are attached form a heterocyclic ring; each R$^{6a}$ is independently selected from:
—OR$^8$,
—NR$^7$S(O)$_m$R$^8$,
—NO$_2$,
halogen,
—S(O)$_m$R$^7$,
—SR$^8$,
—S(O)$_2$OR$^7$,
—OS(O)$_2$R$^8$,
—S(O)$_m$NR$^7$R$^8$,
—NR$^7$R$^8$,
—O(CR$^9$R)$_n$NR$^7$R$^8$,
—C(O)R$^7$,
—CO$_2$R$^8$,
—CO$_2$(CR$^9$R$^{10}$)$_n$CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CR$^7$(N—OR$^8$),
—CF$_2$,
—CF$_3$,
—OCF$_2$, and
—OCF$_3$, each R$^{6b}$ is independently selected from:
R$^{6a}$,
C$_{1-10}$ alkyl,
aryl,
arylC$_{1-4}$ alkyl,
heteroaryl, and
heteroarylC$_{1-4}$ alkyl;

R$^7$ and R$^8$ are independently selected from:
hydrogen,
C$_{1-10}$ alkyl,
C$_{2-10}$ alkenyl,
C$_{2-10}$ alkynyl,
cycloalkyl,
cycloalkyl-C$_{1-10}$ alkyl;
heterocyclyl,
heterocyclyl—C$_{1-10}$ alkyl,
aryl,
heteroaryl,
aryl-C$_{1-10}$ alkyl, and
heteroaryl-C$_{1-10}$ alkyl,
wherein alkyl, alkenyl, alkynyl, cycloalkyl, and heterocyclyl are each unsubstituted or substituted with at least one substituent, such as one, two, three, or four substituents, independently selected from R$^{6a}$, and aryl and heteroaryl are each unsubstituted or substituted with at least one substituent, such as one, two, three, or four substituents, independently selected from R$^{6b}$; or R$^7$ and R$^8$ together with the atom(s) to which they are attached form a heterocyclic ring of 4 to 7 members containing 0, 1, or 2 additional heteroatoms independently selected from oxygen, sulfur and NR$^{11}$, each R$^7$ and R$^8$ may be unsubstituted or substituted on a carbon or nitrogen atom with at least one substituent, such as one, two, or three substituents, selected from R$^{12}$;

R$^9$ and R$^{10}$ are independently selected from hydrogen, C$_{1-10}$ alkyl, C$_{2-10}$ alkenyl, C$_{2-10}$ alkynyl, cycloalkyl, cycloalkyl-C$_{1-10}$ alkyl, heterocyclyl, heterocyclyl —C$_{1-10}$ alkyl, aryl, heteroaryl, aryl-C$_{1-10}$ alkyl, and heteroaryl-C$_{1-10}$ alkyl; or R$^9$ and R$^{10}$ together with the carbon to which they are attached form a ring of 3 to 7 members containing 0, 1, or 2 heteroatoms independently selected from oxygen, sulfur and nitrogen; each R$^{11}$ is independently selected from:
hydrogen,
C$_{1-10}$ alkyl,
C$_{3-8}$ cycloalkyl,
C$_{3-8}$ cycloalkyl-C$_{1-4}$ alkyl,
heterocyclyl,
heterocyclyl-C$_{1-4}$ alkyl,
aryl,
aryl-C$_{1-4}$ alkyl,
heteroaryl,
heteroaryl-C$_{1-4}$ alkyl,
—S(O)$_m$R$^7$,
—C(O)R$^7$,
—CO$_2$R$^7$,
—CO$_2$(CR$^9$R$^{10}$)$_n$CONR$^7$R$^8$, and
—C(O)NR$^7$R$^8$;

each R$^{12}$ is independently selected from:
halogen,
C$_{1-10}$ alkyl,
C$_{3-8}$ cycloalkyl,
C$_{3-8}$ cycloalkylalkyl,
heterocyclyl,
heterocyclylalkyl,
aryl,
arylC$_{1-4}$ alkyl,
heteroaryl,
heteroarylC$_{1-4}$ alkyl,
—OR$^7$,
—NR$^7$S(O)$_m$R$^8$,
—S(O)$_m$R$^7$,
—SR$^7$,
—S(O)$_2$OR$^7$,
—OS(O)$_2$R$^7$,
—S(O)$_m$NR$^7$R$^8$,
—NR$^7$R$^8$,
—O(CR$^9$R$^{10}$)$_n$NR$^7$R$^8$,
—C(O)R$^7$,
—CO$_2$R$^8$, —CO$^2$(CR$^9$R$^{10}$)$_n$CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CF$_2$,
—CF$_3$,
—OCF$_2$, and
—OCF$_3$;

L is a linker selected from:
—CR$^7$R$^8$—,
—O—,
—NR$^7$—,
—S—,
—SO—, and
—SO$_2$—;

m is selected from 1 and 2; and
n is selected from 1, 2, and 3.

Provided is a pharmaceutical composition, which comprises at least one compound and/or at least one pharmaceutically acceptable salt thereof described herein, and at least one pharmaceutically acceptable carrier.

Provided is a method for treating a condition selected from insulin resistance, hyperglycemia, and Type II diabetes comprising administering to a patient in recognized need thereof an effective amount of at least one compound and/or at least one pharmaceutically acceptable salt thereof described herein.

As used herein the following definitions are applicable.

The term "alkyl" refers to both branched and straight-chain saturated aliphatic hydrocarbon groups having the specified number of carbon atoms. Unless otherwise specified, "alkyl" refers to $C_1$-$C_{10}$ alkyl. For example, $C_1$-$C_{10}$, as in "$C_{1-10}$ alkyl" is defined to include groups having 1, 2, 3, 4, 5, 6, 7, 8, 9 or 10 carbons in a linear or branched arrangement. For example, "$C_{1-10}$ alkyl" includes but is not limited to methyl, ethyl, n-propyl, n-butyl, t-butyl, butyl, pentyl, hexyl, heptyl, octyl, nonyl, and decyl.

The term "cycloalkyl" means a saturated aliphatic cyclic hydrocarbon group having the specified number of carbon atoms. Unless otherwise specified, "cycloalkyl" refers to $C_{3-10}$ cycloalkyl. For example, "cycloalkyl" includes but is not limited to cyclopropyl, methyl-cyclopropyl, 2,2-dimethyl-cyclobutyl, 2-ethyl-cyclopentyl, and cyclohexyl.

The term "alkenyl" refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "alkoxy" refers to either a cyclic or non-cyclic alkyl group of indicated number of carbon atoms attached through an oxygen bridge. "Alkoxy" therefore encompasses the definitions of alkyl and cycloalkyl above.

The term "aryl" encompasses:
5- and 6-membered carbocyclic aromatic rings, for example, benzene;
bicyclic ring systems wherein at least one ring is carbocyclic and aromatic, for example, naphthalene, indane, and 1,2,3,4-tetrahydroquinoline; and
tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" (or "halo") refers to fluorine, chlorine, bromine and iodine.

The term "heteroaryl" refers to
5- to 8-membered aromatic, monocyclic rings containing one or more, for example, from 1 to 4, or, in some embodiments, from 1 to 3, heteroatoms selected from N, O, and S, with the remaining ring atoms being carbon;
8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and
11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle" (and variations thereof such as "heterocyclic", or "heterocyclyl") broadly refers to a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

As used herein, "arylalkyl" refers to an alkyl moiety substituted by an aryl group. Example arylalkyl groups include benzyl, phenethyl, and naphthylmethyl groups. In some embodiments, arylalkyl groups have from 7 to 20 or 7 to 11 carbon atoms. When used in the phrase "aryl$C_{1-4}$ alkyl", the term "$C_{1-4}$" refers to the alkyl portion of the moiety and does not describe the number of atoms in the aryl portion of the moiety. Likewise, when used in the phrase "aryl$C_{1-10}$ alkyl", the term "$C_{1-10}$" refers to the alkyl portion of the moiety and does not describe the number of atoms in the aryl portion of the moiety.

As used herein, "heterocyclylalkyl" refers to alkyl substituted by heterocyclyl. When used in the phrase "heterocyclyl$C_{1-10}$ alkyl", the term "$C_{1-10}$" refers to the alkyl portion of the moiety and does not describe the number of atoms in the heterocyclyl portion of the moiety.

As used herein, "cycloalkylalkyl" refers to alkyl substituted by cycloalkyl. When used in the phrase "$C_{3-10}$ cycloalkylalkyl", the term "$C_{3-10}$" refers to the cycloalkyl portion of the moiety and does not describe the number of atoms in the alkyl portion of the moiety. When used in the phrase "$C_{3-7}$ cycloalkylalkyl", the term "$C_{3-7}$" refers to the cycloalkyl portion of the moiety and does not describe the number of atoms in the alkyl portion of the moiety. When used in the phrase "$C_{3-8}$ cycloalkylalkyl", the term "$C_{3-8}$" refers to the cycloalkyl portion of the moiety and does not describe the number of atoms in the alkyl portion of the moiety. When used in the phrase "cycloalkyl $C_{1-10}$ alkyl", the term "$C_{1-10}$" refers to the alkyl portion of the moiety and does not describe the number of atoms in the cycloalkyl portion of the moiety.

As used herein, "heteroarylalkyl" refers to alkyl substituted by heteroaryl. When used in the phrase "heteroaryl $C_{1-4}$ alkyl", the term "$C_{1-4}$" refers to the alkyl portion of the moiety and does not describe the number of atoms in the heteroaryl portion of the moiety. Likewise, when used in the phrase "heteroaryl $C_{1-10}$ alkyl", the term "$C_{1-10}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is arylalkyl, the aryl portion may be unsubstituted or substituted with at least one substituent, such as one, two, three, or four substituents, independently selected from $R^{6b}$ and the alkyl portion may also be unsubstituted or substituted with at least one substituent, such as one, two, three, or four substituents, independently selected from $R^{6a}$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "administration of" and or "administering" at least one compound and/or at least one pharmaceutically acceptable salt should be understood to mean providing at least one compound and/or at least one pharmaceutically acceptable salt thereof to the individual in recognized need of treatment.

The term "effective amount" means the amount of the at least one compound and/or at least one pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

By "pharmaceutically acceptable" it is meant compatible with the other ingredients of the formulation and not unacceptably deleterious to the recipient thereof.

Provided is at least one compound of formula (I):

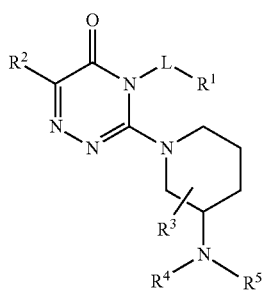

(I)

and/or at least one pharmaceutically acceptable salt thereof, wherein $R^1$ is selected from:
  $C_{1-10}$ alkyl,
  $C_{3-10}$ cycloalkyl,
  $C_{3-10}$ cycloalkylalkyl,
  heterocyclyl,
  heterocyclylalkyl,
  aryl,
  arylalkyl,
  heteroaryl, and
  heteroarylalkyl,
  wherein alkyl, cycloalkyl, and heterocyclyl are each unsubstituted or substituted with at least one substituent, such as one, two, three, or four substituents, independently selected from $R^{6a}$, and wherein aryl and heteroaryl are each unsubstituted or independently substituted with at least one substituent, such as one, two, three, or four substituents, independently selected from $R^{6b}$;

$R^2$ is selected from:
  hydrogen and
  alkyl,
  wherein each alkyl is unsubstituted or substituted with at least one substituent, such as one, two, three, or four substituents, independently selected from $R^{6a}$;

$R^3$ is selected from:
  hydrogen,
  halogen,
  hydroxyl,
  $C_{1-4}$ alkyl,
  $C_{2-4}$ alkenyl,
  $C_{2-4}$ alkynyl,
  $C_{3-7}$ cycloalkyl,
  heterocyclyl,
  $C_{3-7}$ cycloalkylalkyl,
  heterocyclylalkyl,
  aryl,
  heteroaryl,
  arylalkyl, and
  heteroarylalkyl,
  wherein alkyl, alkenyl, alkynyl, cycloalkyl, and heterocyclyl are each unsubstituted or substituted with at least one substituent, such as one, two, three, or four substituents, independently selected from $R^{6a}$, and each aryl and heteroaryl is unsubstituted or substituted with at least one substituent, such as one, two, three, or four substituents, independently selected from $R^{6b}$;

$R^4$ is selected from:
  hydrogen, and
  $C_{1-4}$ alkyl,
  wherein alkyl is unsubstituted or substituted with at least one substituent, such as one, two, three, or four substituents, independently selected from $R^{6a}$;

$R^5$ is selected from:
  hydrogen, and
  $C_{1-4}$ alkyl,
  wherein alkyl is unsubstituted or substituted with at least one substituent, such as one, two, three, or four substituents, independently selected from $R^{6a}$;

or $R^4$ and $R^5$ together with the nitrogen to which they are attached form a heterocyclic ring; each $R^{6a}$ is independently selected from:
  —$OR^8$,
  $NR^7S(O)_mR^8$,
  —$NO_2$,
  halogen, —S(O)$_m$R$^7$,
—SR$^8$,
—S(O)$_2$OR$^7$,
—OS(O)$_2$R$^8$,
—S(O)$_m$NR$^7$R$^8$,
—NR$^7$R$^8$,
—O(CR$^9$R$^{10}$)$_n$NR$^7$R$^8$,
—C(O)R$^7$,
—CO$_2$R$^8$,
—CO$_2$(CR$^9$R$^{10}$)$_n$CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CR$^7$(N—OR$^8$),
—CF$_2$,
—CF$_3$,
—OCF$_2$, and
—OCF$_3$,
each R$^{6b}$ is independently selected from:
  R$^{6a}$,
  C$_{1-10}$ alkyl,
  aryl,
  aryl-C$_{1-4}$ alkyl,
  heteroaryl, and
  heteroaryl-C$_{1-4}$ alkyl;
R$^7$ and R$^8$ are independently selected from:
  hydrogen,
  C$_{1-10}$ alkyl,
  C$_{2-10}$ alkenyl,
  C$_{2-10}$ alkynyl,
  cycloalkyl,
  cycloalkyl-C$_{1-10}$ alkyl;
  heterocyclyl,
  heterocyclyl-C$_{1-10}$ alkyl,
  aryl,
  heteroaryl,
  aryl-C$_{1-10}$ alkyl, and
  heteroaryl-C$_{1-10}$ alkyl,
    wherein alkyl, alkenyl, alkynyl, cycloalkyl, and heterocyclyl are each unsubstituted or substituted with at least one substituent, such as one, two, three, or four substituents, independently selected from R$^{6a}$, and each aryl and heteroaryl are unsubstituted or substituted with at least one substituent, such as one, two, three, or four substituents, independently selected from R$^{6b}$; or
R$^7$ and R$^8$ together with the atom(s) to which they are attached form a heterocyclic ring of 4 to 7 members containing 0, 1, or 2 additional heteroatoms independently selected from oxygen, sulfur and NR$^{11}$,
each R$^7$ and R$^8$ may be unsubstituted or substituted on a carbon or nitrogen atom with at least one substituent, such as one, two, or three substituents, selected from R$^{12}$;
R$^9$ and R$^{10}$ are independently selected from hydrogen, C$_{1-10}$ alkyl, C$_{2-10}$ alkenyl, C$_{2-10}$ alkynyl, cycloalkyl, cycloalkyl-C$_{1-10}$ alkyl, heterocyclyl, heterocyclyl-C$_{1-10}$ alkyl, aryl, heteroaryl, aryl-C$_{1-10}$ alkyl, and heteroaryl-C$_{1-10}$ alkyl; or
R$^9$ and R$^{10}$ together with the carbon to which they are attached form a ring of 3 to 7 members containing 0, 1, or 2 heteroatoms independently selected from oxygen, sulfur and nitrogen; each R$^{11}$ is independently selected from:
  hydrogen,
  C$_{1-10}$ alkyl,
  C$_{3-8}$ cycloalkyl,
  C$_{3-8}$ cycloalkyl-C$_{1-4}$ alkyl,
  heterocyclyl,
  heterocyclyl-C$_{14}$ alkyl,
  aryl,
  aryl-C$_{1-4}$ alkyl,
  heteroaryl,
  heteroaryl-C$_{1-4}$ alkyl,
  —C(O)R$^7$,
  —CO$_2$R$^7$,
  —CO$_2$(CR$^9$R$^{10}$)$_n$—CONR$^7$R$^8$, and
  —C(O)NR$^7$R$^8$;
each R$^{12}$ is independently selected from:
  halogen,
  C$_{1-10}$ alkyl,
  C$_{3-8}$ cycloalkyl,
  C$_{3-8}$ cycloalkylalkyl,
  heterocyclyl,
  heterocyclylalkyl,
  aryl,
  aryl-C$_{1-4}$ alkyl,
  heteroaryl,
  heteroaryl-C$_{1-4}$ alkyl,
  —OR$^7$,
  —NR$^7$S(O)$_m$R$^8$,
  —S(O)$_m$R$^7$,
  —SR$^7$,
  —S(O)$_2$OR$^7$,
  —OS(O)$_2$R$^7$,
  —S(O)$_m$NR$^7$R$^8$,
  —NR$^7$R$^8$,
  —O(CR$^9$R$^{10}$)—NR$^7$R$^8$,
  —C(O)R$^7$,
  —CO$_2$R$^8$,
  —CO$^2$(CR$^9$R$^{10}$)—CONR$^7$R$^8$,
  —OC(O)R$^7$,
  —CN,
  —C(O)NR$^7$R$^8$,
  —NR$^7$C(O)R$^8$,
  —OC(O)NR$^7$R$^8$,
  —NR$^7$C(O)OR$^8$,
  —NR$^7$C(O)NR$^7$R$^8$,
  —CF$_2$,
  —CF$_3$,
  —OCF$_2$, and
  —OCF$_3$;
L is a linker selected from:
  —CR$^7$R$^8$—,
  —O—,
  —NR$^7$—,
  —S—,
  —SO—, and
  —SO$_2$—;
m is selected from 1 and 2; and
n is selected from 1, 2, and 3.
  In some embodiments, L is —CR$^7$R$^8$—.
  In some embodiments, at least one of R$^7$ and R$^8$ is hydrogen.
  In some embodiments, each of R$^7$ and R$^8$ is hydrogen.
  In some embodiments, R$^2$ is alkyl.
  In some embodiments, R$^2$ is methyl.
  In some embodiments, R$^1$ is aryl unsubstituted or substituted with at least one substituent independently selected from R$^{6b}$.
  In some embodiments, R$^1$ is phenyl unsubstituted or substituted with at least one substituent independently selected from R$^{6b}$.

In some embodiments, $R^1$ is phenyl, unsubstituted or substituted with at least one substituent selected from halogen and cyano.

In some embodiments, $R^1$ is selected from 2-cyanophenyl, 2-chloro-5-fluorophenyl, 2-cyano-5-fluorophenyl, and 2-bromo-5-fluorophenyl.

In some embodiments, $R^3$ is hydrogen.
In some embodiments, $R^4$ is hydrogen.
In some embodiments, $R^5$ is hydrogen.

Also provided is least one compound and/or at least one pharmaceutically acceptable salt thereof, selected from
(R)-2-((3-(3-aminopiperidin-1-yl)-6-methyl-5-oxo-1,2,4-triazin-4(5H)-yl)methyl)benzonitrile;
(R)-3-(3-aminopiperidin-1-yl)-4-(2-bromo-5-fluorobenzyl)-6-methyl-1,2,4-triazin-5(4H)-one;
(R)-2-((3-(3-aminopiperidin-1-yl)-6-methyl-5-oxo-1,2,4-triazin-4(5H)-yl)methyl)-4-fluorobenzonitrile;
(R)-3-(3-aminopiperidin-1-yl)-4-(2-chloro-5-fluorobenzyl)-6-methyl-1,2,4-triazin-5(4H)-one, and
pharmaceutically acceptable salts thereof.

Also provided is a method of treating a condition responsive to inhibition of dipeptidyl peptidase-IV enzyme comprising administering to a patient in recognized need thereof an effective amount of the at least one compound and/or at least one pharmaceutically acceptable salt described herein.

Also provided is a method of treating a condition selected from insulin resistance, hyperglycemia, and Type II diabetes comprising administering to a patient in recognized need thereof an effective amount of the at least one compound and/or at least one pharmaceutically acceptable salt described herein.

In some embodiments, the at least one compound and/or at least one pharmaceutically acceptable salt thereof described herein can be useful in a method of inhibiting the dipeptidyl peptidase-IV enzyme in a patient such as a mammal in recognized need of such inhibition comprising the administration of an effective amount of the at least one compound and/or at least one pharmaceutically acceptable salt described herein. Also provided is the use of the at least one compound and/or at least one pharmaceutically acceptable salt thereof described herein as inhibitors of dipeptidyl peptidase-IV enzyme activity.

In addition to primates, such as humans, a variety of other mammals can be treated according to the methods described herein. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Also provided is a composition comprising the at least one compound and/or at least one pharmaceutically acceptable salt described herein and at least one pharmaceutically acceptable carrier.

Also provided is a method for the manufacture of a medicament for inhibiting dipeptidyl peptidase-IV enzyme activity in humans and animals comprising combining at least one compound and/or at least one pharmaceutically acceptable salt described herein with at least one pharmaceutically acceptable carrier.

In some embodiments, the patient is a mammal, such as a human being, male or female, in whom inhibition of dipeptidyl peptidase-IV enzyme activity is desired.

Accordingly, the pharmaceutical compositions described herein encompass any composition made by admixing at least one compound of formula (I) and/or at least one pharmaceutically acceptable salt thereof and at least one pharmaceutically acceptable carrier.

Dipeptidyl peptidase-IV enzyme (DPP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the compounds and/or pharmaceutically acceptable salts described herein can be useful in a method for the treatment of the following diseases, disorders and conditions.

Type II Diabetes and Related Disorders: It is well established that the incretins GLP-1 and GIP are rapidly inactivated in vivo by DPP-IV. Studies with DPP-IV$^{(-/-)}$-deficient mice and preliminary clinical trials indicate that DPP-IV inhibition increases the steady state concentrations of GLP-1 and GIP, resulting, in improved glucose tolerance. By analogy to GLP-1 and GIP, it is likely that other glucagon family peptides involved in glucose regulation are also inactivated by DPP-IV (eg. PACAP). Inactivation of these peptides by DPP-IV may also play a role in glucose homeostasis.

DPP-IV inhibitors described herein therefore may have utility in the treatment of type II diabetes and in the treatment of the numerous conditions that often accompany Type II diabetes, including but being not limited to Syndrome X (also known as Metabolic Syndrome), reactive hypoglycemia, and diabetic dyslipidemia. Obesity, discussed below, is another condition that can be often found with Type II diabetes that may respond to treatment with the DPP-IV inhibitors described herein.

The compounds and/or pharmaceutically acceptable salts described herein may have utility in treating one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated by inhibition of DPP-IV.

Obesity: DPP-IV inhibitors described herein may be useful for the treatment of obesity. This is based on the observed inhibitory effects on food intake and gastric emptying of GLP-1 and GLP-2.

Exogenous administration of GLP-1 in humans significantly decreases food intake and slows gastric emptying (Am. J. Physio., 277: R910-R916 (1999)). ICV administration of GLP-1 in rats and mice also has profound effects on food intake (Nature Medicine, 2: 1254-1258 (1996)).

This inhibition of feeding is not observed in GLP-IR$^{(-/-)}$ mice, indicating that these effects may be mediated through brain GLP-1 receptors. By analogy to GLP-1, it is likely that GLP-2 can be also regulated by DPP-IV. Icy administration of GLP-2 may also inhibit food intake, analogous to the effects observed with GLP-1 (Nature Medicine, 6: 802-807 (2000)). In addition, studies with DPP-IV deficient mice may suggest that these animals are resistant to diet-induced obesity and associated pathology (e.g. hyperinsulinonemia).

Growth Hormone Deficiency: DPP-IV inhibition may be useful for the treatment of growth hormone deficiency, based on the hypothesis that growth-hormone releasing factor (GRF), a peptide that stimulates release of growth hormone from the anterior pituitary, is cleaved by the DPP-IV enzyme in vivo (WO 00/56297). The following data may provide evidence that GRF can be an endogenous substrate: (1) GRF is efficiently cleaved in vitro to generate the inactive product GRF [3-44] (BBA 1122: 147-153 (1992)); (2) GRF is rapidly degraded in plasma to GRF [3-44]; this is prevented by the DPP-IV inhibitor diprotin A; and (3) GRF [3-44] is found in the plasma of a human GRF transgenic pig (J. Clin. Invest., 83: 1533-1540 (1989)). Thus DPP-IV inhibitors may be useful for the same spectrum of indications which have been considered for growth hormone secretagogues.

Intestinal Injury: The potential for using DPP-IV inhibitors for the treatment of intestinal injury can be suggested by the results of studies indicating that glucagon-like peptide-2 (GLP-2), a likely endogenous substrate for DPP-IV, may exhibit trophic effects on the intestinal epithelium (Regulatory Peptides. 90: 27-32 (2000)). Administration of GLP-2 results in increased small bowel mass in rodents and attenuates intestinal injury in rodent models of colitis and enteritis.

Immunosuppression: DPP-IV inhibition may be useful for modulation of the immune response, based upon studies implicating the DPP-IV enzyme in T cell activation and in chemokine processing, and efficacy of DPP-IV inhibitors in in vivo models of disease. DPP-IV has been shown to be identical to CD26, a cell surface marker for activated immune cells. The expression of CD26 can be regulated by the differentiation and activation status of immune cells. It is for example accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-IV. In several cases (RANTES, LD78-beta, MDC, eotaxin, SDF-1 alpha), cleavage can result in an altered activity in chemotaxis and signaling assays.

Receptor selectivity also appears to be modified in some cases (RANTES). Multiple N-terminally truncated forms of a number of chemokines have been identified in in vitro cell culture systems, including the predicted products of DPP-IV hydrolysis.

DPP-IV inhibitors have been shown to be efficacious immunosuppressants in animal models of transplantation and arthritis. Prodipine (Pro-Pro-diphenyl-phosphonate), an irreversible inhibitor of DPP-IV, was shown to double cardiac allograft survival in rats from day 7 to day 14 (Transplantation, 63: 1495-1500 (1997)). DPP-IV inhibitors have been tested in collagen and alkyldiamine-induced arthritis in rats and showed a statistically significant attenuation of hind paw swelling in this model [Int. J. Immunopharmacology, 19: 15-24 (1997) and Immunopharmacology, 40: 21-26 (1998)]. DPP-IV is upregulated in a number of autoimmune diseases including rheumatoid arthritis, multiple sclerosis, Graves' disease, and Hashimoto's thyroiditis (Immunology Today, 20: 367-375 (1999)).

HIV Infection: DPP-IV inhibition may be useful for the treatment of EGV infection or AIDS because a number of chemokines which inhibit HIV cell entry are potential substrates for DPP-IV (Immunology Today 20: 367-375 (1999)). In the case of SDF-1 alpha, cleavage decreases antiviral activity (PNAS, 95: 6331-6 (1998)). Thus, stabilization of SDF-1 alpha through inhibition of DPP-IV would be expected to decrease HTV infectivity.

Hematopoiesis: DPP-IV inhibition may be useful for the treatment of hematopiesis because DPP-IV may be involved in hematopoiesis. A DPP-IV inhibitor, Val-Boro-Pro, stimulated hematopoiesis in a mouse model of cyclophosphamide-induced neutropenia (WO 99/56753).

Neuronal Disorders: DPP-IV inhibition may be useful for the treatment of various neuronal or psychiatric disorders because a number of peptides implicated in a variety of neuronal processes are cleaved in vitro by DPP-IV. A DPP-IV inhibitor thus may have a therapeutic benefit in the treatment of neuronal disorders. Endomorphin-2, beta-casomorphin, and substance P have all been shown to be in vitro substrates for DPP-IV. In an electric shock jump test model of analgesia in rats, a DPP-IV inhibitor showed a significant effect that was independent of the presence of exogenous endomorphin-2 (Brain Research, 815: 278-286 (1999)). Neuroprotective and neuroregenerative effects of DPP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV in vitro and in vivo," Int. Conf. On Dipeptidyl Aminopeptidases: Basic Science and Clinical Applications, Sep. 26-29, 2002 (Berlin, Germany)].

Anxiety rats naturally deficient in DPP-IV have an anxiolytic phenotype (WO 02/34243; Karl et al., Physiol. Behav. 2003). DPP-IV deficient mice also have an anxiolytic phenotype using the Porsolt and light/dark models. Thus DPP-IV inhibitors described herein may prove useful for treating anxiety and related disorders.

Memory and Cognition. GLP-1 agonists can be active in models of learning (passive avoidance, Morris water maze) and neuronal injury (kainate-induced neuronal apoptosis) as demonstrated by During et al. (Nature Med. 9: 1173-1179 (2003)). The results may suggest a physiological role for GLP-1 in learning and neuroprotection. Stabilization of GLP-1 by DPP-IV inhibitors are expected to show similar effects.

Tumor Invasion and Metastasis: DPP-IV inhibition may be useful for the treatment of tumor invasion and metastasis because an increase or decrease in expression of several ectopeptidases including DPP-IV has been observed during the transformation of normal cells to a malignant phenotype (J. Exp. Med., 190: 301-305 (1999)). Up- or down-regulation of these proteins appears to be tissue and cell-type specific. For example, increased CD26/DPP-IV expression has been observed on T cell lymphoma, T cell acute lymphoblastic leukemia, cell-derived thyroid carcinomas, basal cell carcinomas, and breast carcinomas. Thus, DPP-IV inhibitors may have utility in the treatment of such carcinomas.

Benign Prostatic Hypertrophy: DPP-IV inhibition may be useful for the treatment of benign prostatic hypertrophy because increased DPP-IV activity was noted in prostate tissue from patients with BPH (Eur. J. Clin. Chem. Clin. Biochem., 30: 333-338 (1992)).

Sperm motility/male contraception: DPP-IV inhibition may be useful for the altering sperm motility and for male contraception because in seminal fluid, prostatosomes, which are prostate derived organelles important for sperm motility, possess very high levels of DPP-IV activity (Eur. J. Clin. Chem. Clin. Biochem., 30: 333-338 (1992)).

Gingivitis: DPP-IV inhibition may be useful for the treatment of gingivitis because DPP-IV activity was found in gingival crevicular fluid and in some studies correlated with periodontal disease severity (Arch. Oral Biol., 37: 167-173 (1992)).

Osteoporosis: DPP-IV inhibition may be useful for the treatment of osteoporosis because GIP receptors are present in osteoblasts.

The compounds and/or pharmaceutically acceptable salts thereof described herein may be further useful in a method for the treatment of the aforementioned diseases, disorders and conditions in combination with other agents.

The compounds and/or pharmaceutically acceptable salts thereof described herein may be used in combination with one or more other drugs in the treatment of diseases or conditions for which compounds of Formula I and/or pharmaceutically acceptable salts thereof or the other drugs may have utility, particularly where the combination of the drugs together are safer or more effective than either drug alone. Such other drug (s) may be administered, by a route and in an amount commonly used therefore, contemporaneously or sequentially with at least one compound of Formula I and/or at least one pharmaceutically acceptable salt thereof. When at least one compound of Formula I and/or at least one pharmaceutically acceptable salt thereof is used contemporaneously with one or more other drugs, a pharmaceutical composition in unit dosage form containing such at least one drug and the at least one compound of Formula I and/or at least one pharmaceutically acceptable salt thereof may be desired. However, the combination therapy may also include therapies in which the at least one compound of Formula I and/or at least one pharmaceutically acceptable salt thereof and one or more other drugs are administered on different overlapping schedules. It is also contemplated that when used in combination with one or more other active ingredients, the compound(s) described herein and the other active ingredients may be used in lower doses than when each is used singly. Accordingly, the pharmaceutical compositions described herein include but are not limited to those that contain one or more other active ingredients, in addition to at least one compound of Formula I and/or at least one pharmaceutically acceptable salt thereof.

Examples of other active ingredients that may be administered in combination with at least one compound of Formula I and/or at least one pharmaceutically acceptable salt thereof, and either administered separately or in the same pharmaceutical composition, include, but are not limited to: (a) other dipeptidyl peptidase IV (DPP-IV) inhibitors; (b) insulin sensitizers including (i) PPARγ agonists such as the glitazones (e.g., troglitazone, pioglitazone, englitazone, MCC-555, rosiglitazone, balaglitazone, and the like) and other PPAR ligands, including PPARα/γ dual agonists, such as KRP-297 and muraglitazar, and PPARα agonists such as fenofibric acid derivatives (e.g., gemfibrozil, clofibrate, fenofibrate and bezafibrate), (ii) biguanides such as metformin and phenformin, and (iii) protein tyrosine phosphatase-1B (PTP-1B) inhibitors; (c) insulin or insulin mimetics; (d) sulfonylureas and other insulin secretagogues, such as tolbutamide glyburide, glipizide, glimepiride, and meglitinides, such as nateglinide and repaglinide; (e) α-glucosidase inhibitors (such as acarbose and miglitol); (f) glucagon receptor antagonists such as those described in WO 98/04528, WO 99/01423, WO 00/39088, and WO 00/69810; (g) GLP-1, GLP-1 mimetics, such as Exendin 4, and liraglutide, and GLP-1 receptor agonists such as those described in WO 00/42026 and WO 00/59887; (h) GIP and GIP mimetics such as those described in WO 00/58360, and GIP receptor agonists; (i) PACAP, PACAP mimetics, and PACAP receptor agonists such as those described in WO 01/23420; (j) cholesterol lowering agents such as (i) HMG-CoA reductase inhibitors (e.g., lovastatin, simvastatin, pravastatin, cerivastatin, fluvastatin, atorvastatin, itavastatin, and rosuvastatin and other statins, as well as appropriate salts thereof), (ii) sequestrants (e.g., cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (e.g., gemfibrozil, clofibrate, fenofibrate and bezafibrate), (v) PPARα/γ dual agonists, such as KRP-297, (vi) inhibitors of cholesterol absorption, such as β-sitosterol and ezetimibe, (vii) acyl-CoA: cholesterol acyltransferase inhibitors, such as avasimibe, and (viii) anti-oxidants, such as probucol; (k) PPARδ agonists, such as those described in WO 97/28149; (l) antiobesity compounds such as fenfluramine, dexfenfluramine, phentermine, sibutramine, orlistat, neuropeptide Y1 or Y5 antagonists, CB1 receptor inverse agonists and antagonists, adrenergic receptor agonists, melanocortin-receptor agonists, for example, melanocortin-4 receptor agonists, ghrelin antagonists, and melanin-concentrating hormone (MCH) receptor antagonists; (m) ileal bile acid transporter inhibitors; (n) agents intended for use in inflammatory conditions such as aspirin, other non-steroidal anti-inflammatory drugs, such as ibuprofen, glucocorticoids, azulfidine, and selective cyclooxygenase-2 inhibitors; (o) antihypertensive agents such as ACE inhibitors (e.g., enalapril, lisinopril, captopril, quinapril, tandolapril), A-II receptor blockers (e.g., losartan, candesartan, irbesartan, valsartan, telmisartan, eprosartan), beta blockers and calcium channel blockers; and (p) glucokinase activators (GKAs).

Dipeptidyl peptidase-IV inhibitors that can be combined with at least one compound of formula I and/or at least one pharmaceutically acceptable salt thereof include but are not limited to those described in WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181. Exemplary mention can be made of DPP-IV inhibitor compounds such as isoleucine thiazolidide; MK-0431 and SYR-322.

Antiobesity compounds that can be combined with at least one compound of formula I and/or at least one pharmaceutically acceptable salt thereof include but are not limited to fenfluramine, dexfenfluramine, phentermine, sibutramine, orlistat, neuropeptide Y1 or Y5 antagonists, cannabinoid CB1 receptor antagonists or inverse agonists, melanocortin receptor agonists, for example, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," Expert Opin. Ther. Patents, 11: 1677-1692 (2001) and D. Spanswick and K. Lee, "Emerging antiobesity drugs," Expert Opin. Emerging Drugs, 8: 217-237 (2003).

Neuropeptide Y5 antagonists that can be combined with at least one compound of formula I and/or at least one pharmaceutically acceptable salt thereof include but are not limited to those described in U.S. Pat. No. 6,335,345 and WO 01/14376; and exemplary mention can be made of GW 59884A; GW 569180A; LY366377; and CGP-71683A.

Cannabinoid CB1 receptor antagonists that can be combined with at least one compound of formula I and/or at least one pharmaceutically acceptable salt thereof include but are not limited to those described in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with at least one compound of formula I and/or at least one pharmaceutically acceptable salt thereof include but are not limited to those described in WO 03/009847; WO 02/068388; WO 99/64002; WO 00/74679; WO 01/70708; and WO 01/70337 as well as those described in J. D. Speake et al., "Recent advances in the development of melanocortin-4 receptor agonists," Expert Opin. Ther. Patents, 12: 1631-1638 (2002).

The potential utility of safe and effective activators of glucokinase (GKAs) for the treatment of diabetes is discussed in J. Grimsby et al., "Allosteric Activators of Glucokinase: Potential Role in Diabetes Therapy," Science, 301: 370-373 (2003).

When at least one compound and/or at least one pharmaceutically acceptable salt thereof described herein is used contemporaneously with one or more other drugs, in some embodiments, a pharmaceutical composition containing such at least one other drug in addition to the at least one compound and/or at least one pharmaceutically acceptable salt thereof described herein is used. Accordingly, the pharmaceutical compositions described herein include but are not limited to those that also contain one or more other active ingredients, in addition to at least one compound and/or at least one pharmaceutically acceptable salt thereof described herein.

The weight ratio of the at least one compound and/or at least one pharmaceutically acceptable salt thereof described herein to the at least one second active ingredient may be varied and will depend upon the effective dose of each ingredient. For example, an effective dose of each will be used. Thus, for example, when at least one compound and/or at least one pharmaceutically acceptable salt thereof described herein is combined with at least one another agent, the weight ratio of the at least one compound and/or at least one pharmaceutically acceptable salt thereof to the at least one another agent will for example range from 1000:1 to 1:1000, such as from 200:1 to 1:200. Combinations of at least one compound and/or at least one pharmaceutically acceptable salt thereof described herein and other active ingredients will for example also be within the aforementioned range, but in each case, an effective dose of each active ingredient should be used.

In such combinations the at least one compound and/or at least one pharmaceutically acceptable salt thereof described herein and other active agents may be administered separately or in conjunction. In addition, the administration of one element may be prior to, concurrent to, or subsequent to the administration of other agent(s).

The at least one compound and/or at least one pharmaceutically acceptable salt thereof described herein may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the at least one compound and/or at least one pharmaceutically acceptable salt thereof described herein may be effective for use in humans.

The pharmaceutical compositions for the administration of the at least one compound and/or at least one pharmaceutically acceptable salt thereof described herein may conveniently be presented in dosage unit form and may be prepared by any of the methods well known in the art of pharmacy. In some embodiments, the at least one compound and/or at least one pharmaceutically acceptable salt thereof described herein is brought into association with the carrier which constitutes one or more accessory ingredients.

In some embodiments, the pharmaceutical compositions are prepared by uniformly and intimately bringing the at least one compound and/or at least one pharmaceutically acceptable salt thereof described herein into association with a liquid carrier or a finely divided solid carrier or both, and then, if necessary, shaping the product into the desired formulation. In some embodiments, the at least one compound and/or at least one pharmaceutically acceptable salt thereof described herein is included in an amount sufficient to produce the desired effect upon the process or condition of diseases.

The pharmaceutical compositions containing the at least one compound and/or at least one pharmaceutically acceptable salt thereof described herein may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate, and sodium phosphate; granulating and disintegrating agents, for example, corn starch, and alginic acid; binding agents, for example starch, gelatin, and acacia, and lubricating agents, for example magnesium stearate, stearic acid, and talc. The tablets may be uncoated or they may be coated by known techniques to delay disintegration and absorption in the gastrointestinal tract and thereby provide a sustained action over a longer period. For example, a time delay material, such as glyceryl monostearate and glyceryl distearate may be employed. They may also be coated by the techniques described in the U.S. Pat. Nos. 4,256,108; 4,166,452; and 4,265,874 to form osmotic therapeutic tablets for controlled, such as sustained or delayed, release.

Formulations for oral use may also be presented as hard gelatin capsules wherein the at least one compound and/or at least one pharmaceutically acceptable salt thereof described herein is mixed with an inert solid diluent, for example, calcium carbonate, calcium phosphate and/or kaolin, or as soft gelatin capsules wherein the at least one compound and/or at least one pharmaceutically acceptable salt thereof described herein is mixed with water or an oil medium, for example peanut oil, liquid paraffin, and/or olive oil.

Salts, such as sodium salts, of the DPP-IV inhibitors described herein may be prepared with carriers that protect the at least one compound and/or at least one pharmaceutically acceptable salt thereof described herein against rapid elimination from the body, such as time release formulations or coatings. The formulations may further include other active compounds to obtain desired combinations of properties.

Oral pharmaceutical dosage forms may be solid, gel or liquid. Examples of solid dosage forms include, but are not limited to, tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, DPP-IV inhibitors described herein are provided as solid dosage forms, such as capsules and tablets. The tablets, pills, capsules, troches, and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium, and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar, and carboxymethylcellulose.

Examples of coloring agents that may be used include, but are not limited to, any of the approved certified water soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac, and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the at least one compound of formula I and/or at least one pharmaceutically acceptable salt thereof described herein may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

The at least one compound and/or at least one pharmaceutically acceptable salt thereof described herein may also be administered as a component of an elixir, suspension, syrup, wafer, sprinkle, chewing gum or the like. A syrup may optionally comprise, in addition to the at least one compound and/or at least one pharmaceutically acceptable salt thereof described herein, sucrose as a sweetening agent and certain preservatives, dyes and colorings, and flavors.

The at least one compound and/or at least one pharmaceutically acceptable salt thereof described herein may also be mixed with other active materials that do not impair the desired action, or with materials that supplement the desired action, such as antacids, H2 blockers, and diuretics. For example, if at least one compound and/or at least one pharmaceutically acceptable salt thereof described herein is used for treating asthma or hypertension, it may be used with other bronchodilators and antihypertensive agents, respectively.

Examples of pharmaceutically acceptable carriers that may be included in tablets comprising at least one compound and/or at least one pharmaceutically acceptable salt thereof described herein include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions, and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be, but are not limited to, oil-in-water or water-in-oil emulsions. Examples of pharmaceutically acceptable carriers that may be used in emulsions include, but are not limited to non-aqueous liquids, emulsifying agents, and preservatives.

Examples of pharmaceutically acceptable substances that may be used in non-effervescent granules, to be reconstituted into a liquid oral dosage form, include diluents, sweeteners, and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Exemplary examples of preservatives that may be used include glycerin, methyl and propylparaben, benzoic add, sodium benzoate, and alcohol.

Exemplary examples of non-aqueous liquids that may be used in emulsions include mineral oil and cottonseed oil.

Exemplary examples of emulsifying agents that may be used include gelatin, acacia, tragacanth, bentonite, and surfactants such as polyoxyethylene sorbitan monooleate.

Exemplary examples of suspending agents that may be used include sodium carboxymethylcellulose, pectin, tragacanth, Veegum, and acacia. Diluents include lactose and sucrose. Sweetening agents include sucrose, syrups, glycerin, and artificial sweetening agents, such as sodium cyclamate and saccharin.

Exemplary examples of wetting agents that may be used include propylene glycol monostearate, sorbitan monooleate, diethylene glycol monolaurate, and polyoxyethylene lauryl ether.

Exemplary examples of organic acids that may be used include citric and tartaric acid.

Sources of carbon dioxide that may be used in effervescent compositions include sodium bicarbonate and sodium carbonate. Coloring agents include any of the approved certified water soluble ED and C dyes, and mixtures thereof Exemplary examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is, for example, encapsulated in a gelatin capsule. Such solutions, and the preparation and encapsulation thereof, are described in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells.

Also provided are compositions designed to administer the at least one compound and/or at least one pharmaceutically acceptable salt thereof described herein by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables include, but are not limited to water, saline, dextrose, glycerol, and ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins. Implantation of a slow-release or sustained-release system, such that a constant level of dosage is maintained (see, e.g., U.S. Pat. No. 3,710,795) is also contemplated herein. The percentage of the at least one compound and/or at least one pharmaceutically acceptable salt thereof described herein contained in such parenteral compositions is highly dependent on the specific nature thereof, as well as the activity of the at least one compound and/or at least one pharmaceutically acceptable salt thereof described herein and the needs of the patient.

Parenteral administration of the formulations includes intravenous, subcutaneous, and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous.

When administered intravenously, examples of suitable carriers include, but are not limited to, physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering and chelating agents, and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil, and peanut oil.

Antimicrobial agents in bacteriostatic or fungistatic concentrations may be added to parenteral preparations, particularly when the preparations are packaged in multiple-dose containers and thus designed to be stored and multiple aliquots to be removed there from. Examples of antimicrobial agents that may used include phenols and cresols, mercurials, benzyl alcohol, chlorobutanol, methyl and propyl p-hydroxybenzoic acid esters, thimerosal, benzalkonium chloride, and benzethonium chloride.

Examples of isotonic agents that may be used include sodium chloride and dextrose. Examples of buffers that may be used include phosphate and citrate Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose, and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles, and sodium hydroxide, hydrochloric acid, citric acid, and lactic acid for pH adjustment.

The concentration of the at least one compound and/or at least one pharmaceutically acceptable salt thereof described herein in the parenteral formulation may be adjusted so that an injection administers a pharmaceutically effective amount sufficient to produce the desired pharmacological effect. The exact concentration of the at least one compound and/or at least one pharmaceutically acceptable salt thereof described herein and/or dosage to be used will ultimately depend on the age, weight, and condition of the patient or animal as is known in the art.

Unit-dose parenteral preparations may be packaged in an ampoule, a vial, or a syringe with a needle. AU preparations for parenteral administration should be sterile, as is known and practiced in the art.

Injectables may be designed for local and systemic administration. For example, a therapeutically effective dosage is formulated to contain a concentration of at least about 0.1% w/w up to about 90% w/w or more, such as more than 1% w/w of the at least one compound and/or at least one pharmaceutically acceptable salt thereof described herein to the treated tissue(s). The at least one compound and/or at least one pharmaceutically acceptable salt thereof described herein may be administered at once, or may be divided into a number of smaller doses to be administered at intervals of time. It is understood that the precise dosage and duration of treatment will be a function of the location of where the composition is parenterally administered, the carrier, and other variables that may be determined empirically using known testing protocols or by extrapolation from in vivo or in vitro test data. It is to be noted that concentrations and dosage values may also vary with the age of the individual treated. It is to be further understood that for any particular patient, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The at least one compound and/or at least one pharmaceutically acceptable salt thereof described herein may optionally be suspended in micronized or other suitable form or may be derivatized to produce a more soluble active product. The form of the resulting mixture depends upon a number of factors, including the intended mode of administration and the solubility of the compound in the selected carrier or vehicle. The effective concentration is sufficient for ameliorating the symptoms of the disease state and may be empirically determined.

The at least one compound and/or at least one pharmaceutically acceptable salt thereof described herein may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose, or other suitable agent, about 1-20%, such as about 5 to 15%, in a suitable buffer, such as citrate, sodium, and/or potassium phosphate and/or other such buffer known to those of skill in the art at, typically, about neutral pH. Then, the at least one compound and/or at least one pharmaceutically acceptable salt thereof described herein is added to the resulting mixture, for example, above room temperature, such as at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the at least one compound and/or at least one pharmaceutically acceptable salt thereof described herein.

The at least one compound and/or at least one pharmaceutically acceptable salt thereof described herein may also be administered as topical mixtures. Topical mixtures may be used for local and systemic administration. The resulting mixture may be a solution, suspension, emulsion, or the like and is formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration. The at least one compound and/or at least one pharmaceutically acceptable salt thereof described herein may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will for example have median diameters of less than 50 microns, such as less than 10 microns.

The at least one compound and/or at least one pharmaceutically acceptable salt thereof described herein may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the at least one compound and/or at least one pharmaceutically acceptable salt thereof described herein alone or in combination with other pharmaceutically acceptable excipients can also be administered.

Depending upon the disease state being treated, other routes of administration, such as topical application, transdermal patches, and rectal administration, may also be used. For example, pharmaceutical dosage forms for rectal administration are rectal suppositories, capsules, and tablets for systemic effect. Rectal suppositories, as used herein, mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

In the treatment of conditions which require inhibition of dipeptidyl peptidase-IV enzyme activity an appropriate dosage level will generally be about 0.1 to 1000 mg per day which can be administered in single or multiple doses.

For example, the dosage level will be about 0.1 to about 250 mg per day; such as from about 0.5 to about 100 mg per day. A suitable dosage level may be about 0.1 to 1000 mg per day, about 0.1 to 500 mg per day, or about 0.1 to 50 mg per day. Within this range the dosage may be 0.1 to 0.5, 0.5 to 5 or 5 to 50 mg per day. For oral administration, the compositions are for example provided in the form of tablets containing 1.0 to 1000 mg of the at least one compound and/or at least one pharmaceutically acceptable salt thereof described herein, such as 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the at least one compound and/or at least one pharmaceutically acceptable salt thereof described herein for the symptomatic adjustment of the dosage to the patient to be treated. The at least one compound and/or at least one pharmaceutically acceptable salt thereof described herein may be administered on a regimen of 1 to 4 times per day, such as once or twice per day.

When treating diabetes mellitus and/or hyperglycemia or hypertriglyceridemia or other diseases for which the at least one compound and/or at least one pharmaceutically acceptable salt thereof described herein are indicated, generally satisfactory results may be obtained when the at least one compound and/or at least one pharmaceutically acceptable salt thereof described herein are administered at a daily dosage of, for example, from about 0.1 mg to about 3000 mg, for example given as a single daily dose or in divided doses two to six times a day, or in sustained release form. For most large mammals, the total daily dosage may be from about 1.0 mg to about 1000 mg, such as from about 1 mg to about 50 mg. In the case of a 70 kg adult human, the total daily dose may generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the at least one compound and/or at least one pharmaceutically acceptable salt thereof described herein employed, the metabolic stability and length of action of that at least one compound and/or at least one pharmaceutically acceptable salt thereof described herein, the age, body weight, general health, sex, diet, mode and time of administration, rate of excretion, drug combination, the severity of the particular condition, and the host undergoing therapy.

Inhibition constants may, for example, be determined as follows. A continuous fluorometric assay is employed with the substrate Gly-Pro-AMC, which is cleaved by DPP-IV to release the fluorescent AMC leaving group. A typical reaction contains approximately 50 pM enzyme, 50 µM Gly-Pro-AMC, and buffer (100 mM HEPES, pH 7.5, 0.1 mg/ml BSA) in a total reaction volume of 100 µL. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for the at least one compound and/or at least one pharmaceutically acceptable salt thereof described herein, solutions of the at least one compound and/or at least one pharmaceutically acceptable salt thereof described herein in DMSO were added to reactions containing enzyme and substrate (final DMSO concentration is 1%). All experiments were conducted at room temperature using the standard reaction conditions described above. To determine the dissociation constants (IC), reaction rates were fit by non-linear regression to the Michaelis-Menton equation for competitive inhibition. The errors in reproducing the dissociation constants are typically less than two-fold.

For example, the at least one compound and/or at least one pharmaceutically acceptable salt thereof of the following examples had activity in inhibiting the dipeptidyl peptidase-IV enzyme in the aforementioned assays, generally with an $IC_{50}$ of less than about 1 µM. Such a result is indicative of the intrinsic activity of the at least one compound and/or at least one pharmaceutically acceptable salt thereof described herein in use as inhibitors of the dipeptidyl peptidase-IV enzyme activity.

Several methods for preparing the at least one compound of formula I and/or at least one pharmaceutically acceptable salt thereof are illustrated in the following Schemes and Examples without limiting the scope of the present disclosure. Starting materials are made according to procedures known in the art or as illustrated herein.

EXAMPLES

Preparation of DPP-IV Inhibitors

Various methods may be developed for synthesizing the at least one compound of formula I and/or at least one pharmaceutically acceptable salt thereof. Representative methods for synthesizing the at least one compound of formula I and/or at least one pharmaceutically acceptable salt thereof are provided in the Examples. It is noted, however, that the at least one compound of formula I and/or at least one pharmaceutically acceptable salt thereof may also be synthesized by other synthetic routes that others may devise.

It will be readily recognized that certain compounds of formula I have atoms with linkages to other atoms that confer a particular stereochemistry to the compound (e.g., chiral centers). It is recognized that synthesis of the at least one compound of formula I and/or at least one pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

The at least one compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the at least one compound of formula (I) and/or at least one pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

The at least one compound of formula I and/or at least one pharmaceutically acceptable salt thereof may be conveniently prepared, or as solvates (e.g. hydrates). Hydrates of the at least one compound of formula I and/or at least one pharmaceutically acceptable salt thereof may be conveniently prepared by recrystallization from an aqueous/organic solvent mixture, using organic solvents such as dioxin, tetrahydrofuran and/or methanol.

The compounds of formula (I) can also be prepared as their individual stereoisomers by reacting a racemic mixture of the compounds with an optically active resolving agent to form a pair of diastereoisomeric compounds, separating the diastereomers, and recovering the optically pure enantiomer. While resolution of enantiomers can be carried out using covalent diasteromeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, for example, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Tr (retention time); RP (reverse phase); MeOH (methanol); i-PrOH (isopropanol); TEA (triethylamine); TFA (trifluoroacetic acid); TFAA (trifluoroacetic anhydride); THF (tetrahydrofuran); DMSO (dimethyl sulfoxide); EtOAc (ethyl acetate); DME (1,2-dimethoxyethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimino); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimino); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); Et (ethyl); tBu (tert-butyl); HPLC (high pressure liquid chomatography); BOP (bis(2-oxo-3-oxazolidinyl)phosphinic chloride); TBAF (tetra-n-butylammonium fluoride); mCPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm E Merck silica gel plates (60F-254), visualized with UV light, 5% ethanolic phosphomolybdic acid, Ninhydrin, or p-anisaldehyde solution. Flash column chromatography was performed on silica gel (230-400 mesh, Merck).

Synthetic Schemes

The at least one compound of formula I and/or at least one pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example, see T. W. Greene and P. G. M. Wuts in "Protective Groups in Organic Chemistry" John Wiley and Sons, 1991.

Synthetic methods for preparing the compounds in the present disclosure are illustrated in the following Schemes and Examples. Starting materials are commercially available or may be made according to procedures known in the art or as illustrated herein.

Compounds of formula I may be prepared by reacting intermediate II with substituted amino piperidine of formula III as illustrated in Scheme 1, wherein $R^1$, $R^2$, $R^3$, $R^4$, $R^5$ and L are as defined above. Amino piperidines of formula III are known in the literature or may be conveniently prepared by a variety of methods familiar to those skilled in the art. Y is a leaving group such as halogen, alkyl sulfide, alkyl sulfoxide or alkyl sulfone.

SCHEME 1

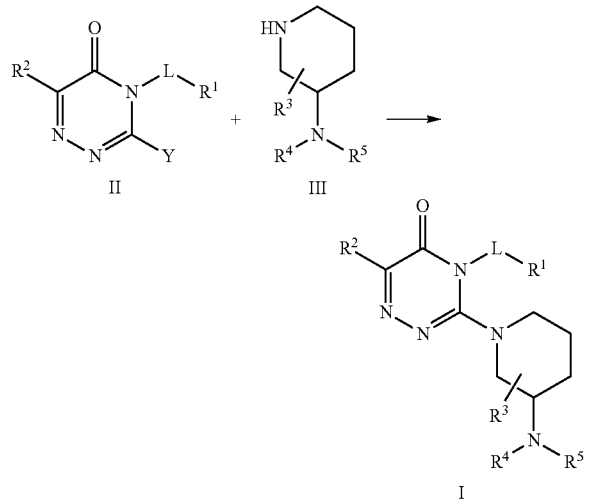

Compounds of formula IIa may be prepared from intermediate VI using a route described in Scheme 2. Intermediates of formula VI are known in the literature or may be conveniently prepared by a variety of methods familiar to those skilled in the art. Reaction of a ketone ester IV with thiosemicarbazide V provides intermediate VI. Cyclization of intermediate VI in a solvent such as water in the presence of a base such as sodium bicarbonate gives triazinone VII. Treatment of triazinone VII with methyl iodide leads to compound VIII. Reaction of compound VIII with electrophiles of formula IX such as alkyl halides gives intermediate IIa.

SCHEME 2

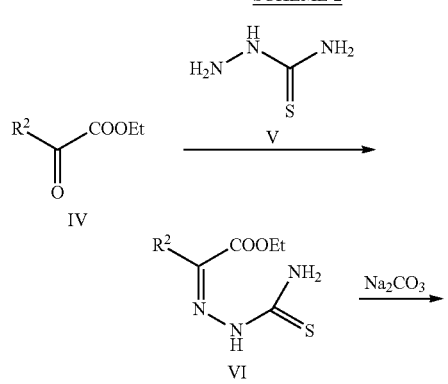

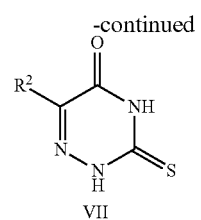

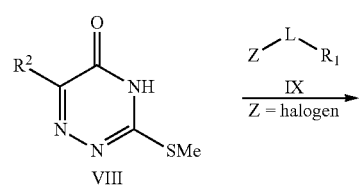

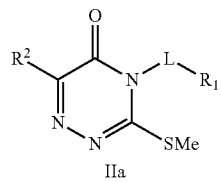

Alternatively, IIa may be prepared from intermediate X as illustrated in Scheme 3. Intermediates of formula X are known in the literature or may be conveniently prepared by a variety of methods familiar to those skilled in the art. Cyclization of intermediate X in a solvent such as toluene in the presence of a base such as DBU leads to compound XI. Treatment of compound XI with methyl iodide gives compound IIa as shown in Scheme 3.

SCHEME 3

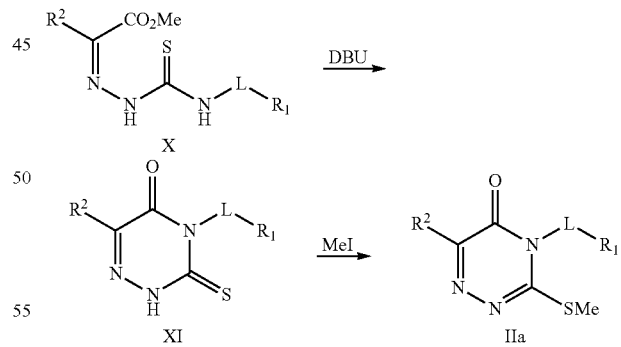

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example 1

(R)-2-((3-(3-aminopiperidin-1-yl)-6-methyl-5-oxo-1,2,4-triazin-4(5H)-yl)methyl)benzonitrile

Step A. 2-(2-carbamothioylhydrazono)propanoic acid (3)

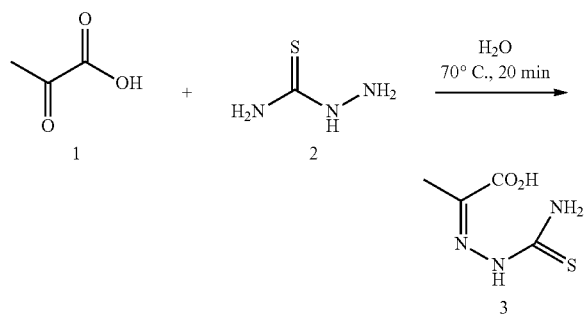

To a mixture of thiosemicarbazide (2) (4.55 g, 50.0 mmol) in water (90 mL) was added pyruvic acid (1) (4.40 g, 50.0 mmol). The mixture was heated at 70° C. for 20 min (while a white solid precipitated). After cooling to room temperature, the white solid was collected by filtration, washed with water and dried in air to give 2-(2-carbamothioylhydrazono)propanoic acid (3).

Step B. 6-methyl-3-thioxo-3,4-dihydro-1,2,4-triazin-5(2H)-one (4)

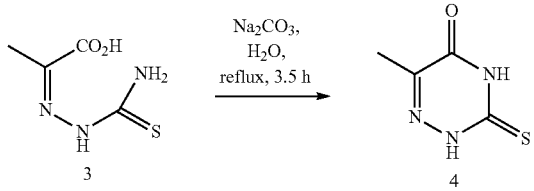

To a solution of $Na_2CO_3$ (4.84 g, 45.6 mmol) in water (300 mL) was added 2-(2-carbamothioylhydrazono)propanoic acid (3, 7.35 g, 45.6 mmol). The mixture was heated at refluxing temperature for 3.5 h. After cooling to room temperature, the clear solution was acidified with 2 N HCl to pH~5. The mixture was extracted with EtOAc (60 mL×4) and $CH_2Cl_2$ (60 mL×4). The combined extracts were dried over $Na_2SO_4$ and concentrated to give 6-methyl-3-thioxo-3,4-dihydro-1,2,4-triazin-5(2H)-one (4) as a white solid. MS: m/z, 144 (100%, M+1).

Step C. 6-methyl-3-(methylthio)-1,2,4-triazin-5(4H)-one (5)

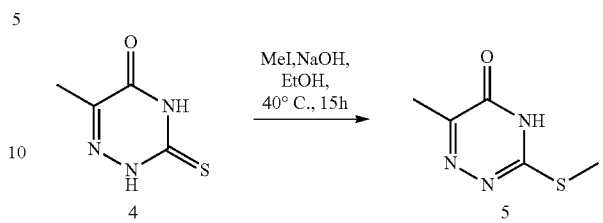

To a solution of 6-methyl-3-thioxo-3,4-dihydro-1,2,4-triazin-5(2H)-one (4, 5.80 g, 40.6 mmol) in absolute ethanol (250 mL) was added NaOH (1.96 g, 49.1 mmol) followed by MeI (11.5 g, 81.2 mmol). The mixture was heated at 40° C. for 15 h. Most of the solvent was evaporated under reduced pressure. Water was added to the residue. The precipitated white solid was collected by filtration and washed with ethanol to give 5 (3.06 g). The aqueous phase was extracted with $CH_2Cl_2$ (80 mL×4). The combined extracts were dried over $Na_2SO_4$ and concentrated to give 3.34 g crude product. This was purified by column chromatography on silica gel, and eluted with 1:1 to 1:2 petroleum ether-ethyl acetate to provide 6-methyl-3-(methylthio)-1,2,4-triazin-5(4H)-one (5). MS: m/z, 158 (100%, M+1).

Step D. 2-((6-methyl-3-(methylthio)-5-oxo-1,2,4-triazin-4(5H)-yl)methyl)benzonitrile (6)

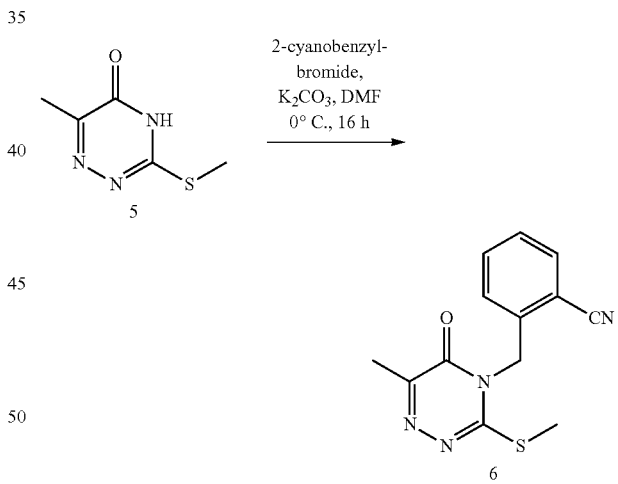

To a solution of 6-methyl-3-(methylthio)-1,2,4-triazin-5(4H)-one (5, 1.546 g, 9.85 mmol) in dry DMF (10 mL) at 0° C. was added $K_2CO_3$ (1.36 g, 9.85 mmol) and 2-cyanobenzylbromide (2.316 g, 11.82 mmol). The mixture was heated at 0° C. for 16 h. The mixture was diluted with water, and extracted with EtOAc (50 mL×3). The combined extracts were washed with brine, dried over $MgSO_4$, and concentrated. This was purified by column chromatography on silica gel, and eluted with 20% to 50% ethyl acetate in petroleum ether and 1:1:2 petroleum ether-dichloromethane-ethyl acetate to provide 2-((6-methyl-3-(methylthio)-5-oxo-1,2,4-triazin-4(5H)-yl)methyl)benzonitrile (6). MS: m/z, 273 (100%, M+1), 295 (60%, M+23).

Step E. (R)-tert-butyl 1-(4-(2-cyanobenzyl)-6-methyl-5-oxo-4,5-dihydro-1,2,4-triazin-3-yl)piperidin-3-ylcarbamate (7)

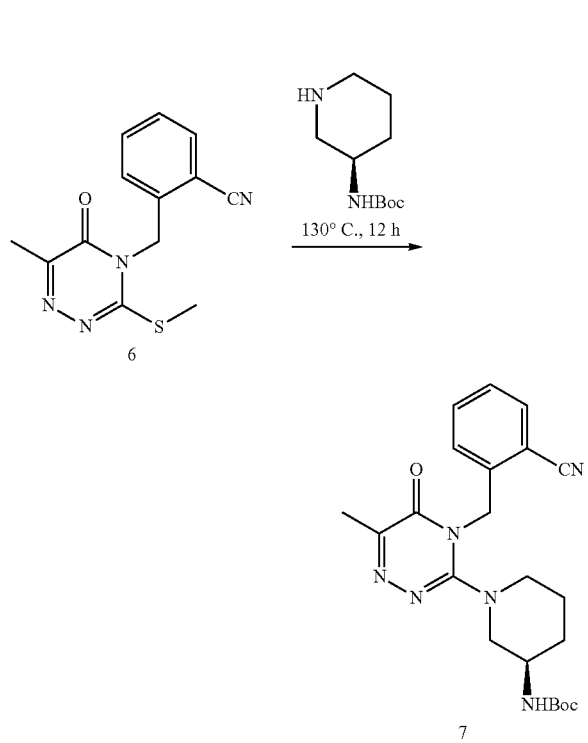

The mixture of 2-((6-methyl-3-(methylthio)-5-oxo-1,2,4-triazin-4(5H)-yl)methyl)benzonitrile (6, 68 mg, 0.25 mmol) and (R)-tert-butyl piperidin-3-ylcarbamate (60 mg, 0.30 mmol) was ground for 5 min and then heated in a tube under nitrogen atmosphere at 130° C. for 13 h. The mixture was separated by silica gel column, and eluted with 2:1 to 1:1 petroleum ether-ethyl acetate and then with 1:1:2 petroleum ether-dichloromethane-ethyl acetate to give (R)-tert-butyl 1-(4-(2-cyanobenzyl)-6-methyl-5-oxo-4,5-dihydro-1,2,4-triazin-3-yl)piperidin-3-ylcarbamate (7). MS: m/z, 425 (100%, M+1), 447(40%, M+23).

Step F. (R)-2-((3-(3-aminopiperidin-1-yl)-6-methyl-5-oxo-1,2,4-triazin-4(5H)-yl)methyl)benzonitrile (8)

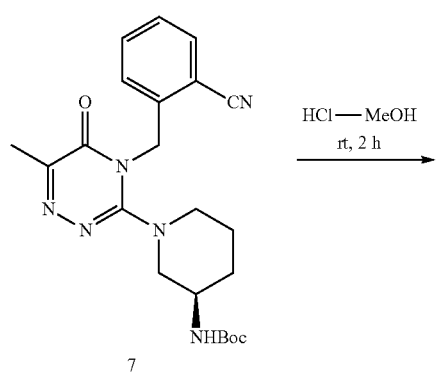

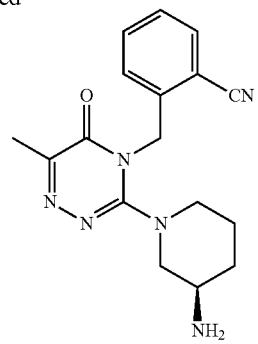

To a solution of (R)-tert-butyl 1-(4-(2-cyanobenzyl)-6-methyl-5-oxo-4,5-dihydro-1,2,4-triazin-3-yl)piperidin-3-ylcarbamate (7, 13 mg) in dichloromethane (0.5 mL) was added HCl in methanol (20%) (1 mL) and the mixture was stirred at RT for 2 h. The mixture was carefully neutralized with NaHCO$_3$ (aq, saturated), and extracted with CH$_2$Cl$_2$ (50 mL×3). The combined extracts were dried over Na$_2$SO$_4$ and concentrated to give the crude product. This was purified by column chromatography on silica gel, eluted with 92:6:2 dichloromethane-methanol-ammonia to provide (R)-2-((3-(3-aminopiperidin-1-yl)-6-methyl-5-oxo-1,2,4-triazin-4(5H)-yl)methyl)benzonitrile (8). MS: m/z, 325 (100%, M+1).

Example 2

(R)-3-(3-aminopiperidin-1-yl)-4-(2-bromo-5-fluorobenzyl)-6-methyl-1,2,4-triazin-5(4H)-one

Step A. Methyl 2-bromo-5-fluorobenzoate (10)

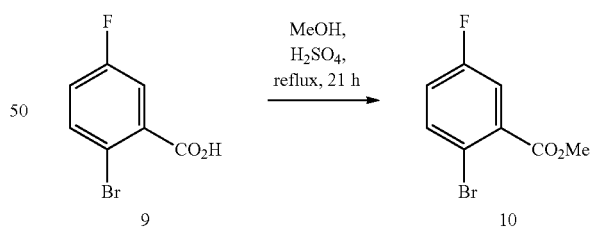

To a solution of 2-bromo-5-fluorobenzoic acid (9) (21.90 g, 100 mmol) in methanol (100 mL) was added conc. H$_2$SO$_4$ (2 mL). The mixture was heated at reflux for 21 h. Most of the solvent was evaporated and diluted with water (200 mL). The mixture was extracted with EtOAc (150 mL×2). The combined extracts were washed with saturated NaHCO$_3$ and brine, dried over MgSO$_4$, and concentrated to give methyl 2-bromo-5-fluorobenzoate (10).

Step B. (2-bromo-5-fluorophenyl)methanol (11)

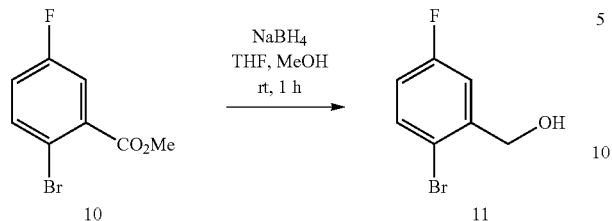

To a solution of methyl 2-bromo-5-fluorobenzoate (10, 21.30 g, 91.4 mmol) in dry THF (150 mL) was added NaBH$_4$ (6.95 g, 183 mmol). Methanol (20 mL) was added dropwise at RT. After the addition, the mixture was stirred at RT for 1 h. Water (200 mL) was slowly added. The mixture was extracted with CH$_2$Cl$_2$ (100 mL×2). The combined extracts were washed with saturated NaHCO$_3$ and brine, dried over MgSO$_4$ and concentrated to give (2-bromo-5-fluorophenyl)methanol (11).

Step C. 1-bromo-2-(bromomethyl)-4-fluorobenzene (12)

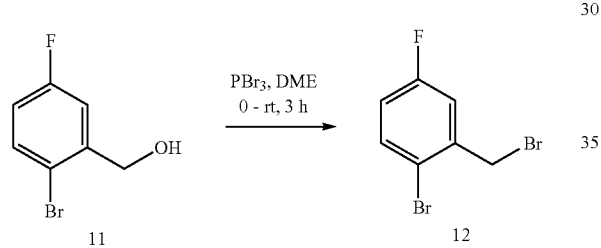

To a solution of (2-bromo-5-fluorophenyl)methanol (11, 4.10 g, 20.0 mmol) in dry DME (40 mL) at 0° C. was added a solution of PBr$_3$ (3.25 g, 12.0 mmol) in dry DME (40 mL) dropwise. The mixture was then slowly warmed up to RT and stirred at for another 3 h. The mixture was diluted with water (100 mL), and extracted with 1:1 petroleum-ether-EtOAc (100 mL×2). The combined extracts were washed with saturated NaHCO$_3$ and brine, dried over MgSO$_4$ and concentrated to give 1-bromo-2-(bromomethyl)-4-fluorobenzene (12).

Step D.
1-bromo-4-fluoro-2-(isothiocyanatomethyl)benzene (13)

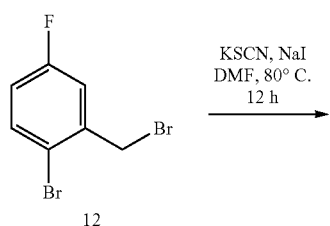

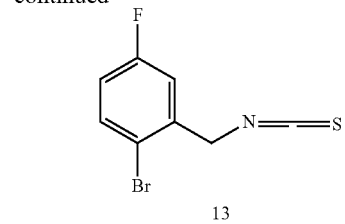

To a solution of 1-bromo-2-(bromomethyl)-4-fluorobenzene (12, 5.36 g, 20.0 mmol) in dry DMF (20 mL) was added NaI (1.20 g, 8.00 mmol) and KSCN (3.88 g, 40.0 mmol). The mixture was heated under N$_2$ at 80° C. for 12 h. After cooling to RT, the mixture was diluted with water (100 mL), and extracted with EtOAc (50 mL×2). The combined extracts were washed with brine, dried over MgSO$_4$ and concentrated to give crude product. This was purified by column chromatography on silica gel, and eluted with petroleum ether to provide 1-bromo-4-fluoro-2-(isothiocyanatomethyl)benzene (13).

Step E.
N-(2-bromo-5-fluorobenzyl)hydrazinecarbothioamide (14)

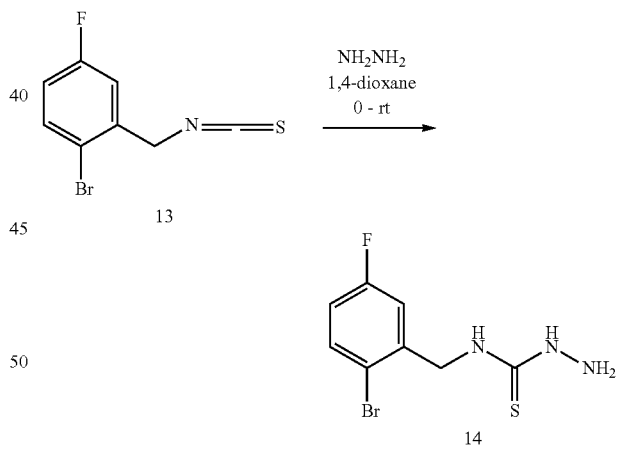

To a solution of hydrazine hydrate (80%, 2.22 g, 35.5 mmol) in 1,4-dioxane (20 mL) at 0° C. was added a solution of 1-bromo-4-fluoro-2-(isothiocyanatomethyl)benzene (13, 3.16 g, 12.8 mmol) in 1,4-dioxane (5 mL) The mixture was stirred at RT for 2 h. Ice cold water (100 mL) was added. The precipitated solid was collected by filtration, washed with water, and dried over P$_2$O$_5$ overnight to provide N-(2-bromo-5-fluorobenzyl)hydrazinecarbothioamide (14). MS: m/z, 278 (100%, M+1), 280 (100%), 300 (10%, M+23), 302 (10%).

Step F. Methyl 2-(2-(2-bromo-5-fluorobenzylcarbamothioyl)hydrazono)propanoate (15)

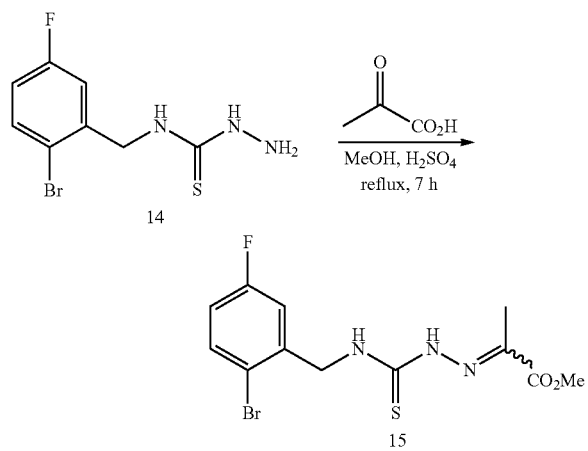

To a solution of pyruvic acid (352 mg, 4.00 mmol) in methanol (15 mL) was added N-(2-bromo-5-fluorobenzyl)hydrazinecarbothioamide (14, 1.112 g, 4.00 mmol) followed by conc. $H_2SO_4$ (5 drops). The mixture was heated at reflux for 7 h. Most of the solvent was evaporated. The residue was taken into EtOAc (150 mL), washed with water, saturated $NaHCO_3$ and brine, dried over $MgSO_4$, and concentrated to give methyl 2-(2-(2-bromo-5-fluorobenzylcarbamothioyl)hydrazono)propanoate (15). MS: m/z, 362 (100%, M+1), 364 (100%), 384 (60%, M+23), 386 (60%).

Step G. 4-(2-bromo-5-fluorobenzyl)-6-methyl-3-thioxo-3,4-dihydro-1,2,4-triazin-5(2H)-one (16)

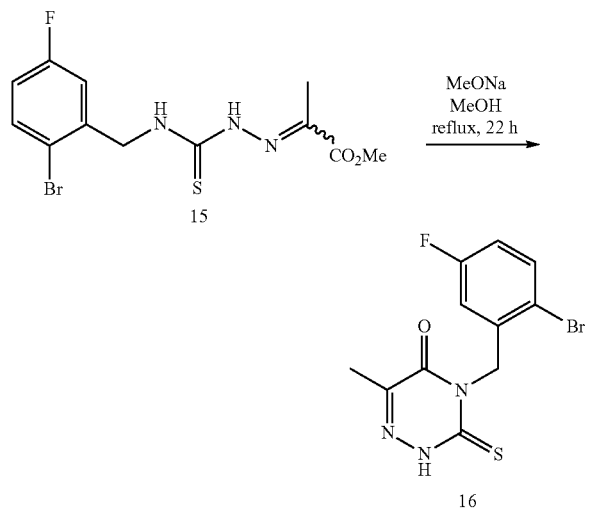

To a solution of MeONa (0.4 M) in methanol (30 mL), freshly prepared from sodium (273 mg, 11.88 mmol) and dry methanol (30 mL), was added methyl 2-(2-(2-bromo-5-fluorobenzylcarbamothioyl)hydrazono)propanoate (15, 1.434 g, 3.96 mmol). The mixture was heated at reflux for 22 h. Most of the solvent was evaporated. The residue was diluted with water (100 mL), acidified with 2 N HCl to pH=1~2, and then extracted with EtOAc (50 mL×2). The extracts were washed with brine, dried over $MgSO_4$, and concentrated to give a mixture which was separated by silica gel column, and eluted with 20-30% ethyl acetate in petroleum ether to give 4-(2-bromo-5-fluorobenzyl)-6-methyl-3-thioxo-3,4-dihydro-1,2,4-triazin-5(2H)-one (16). MS: m/z, 330 (65%, M+1), 332 (60%, M+23).

Step H. 4-(2-bromo-5-fluorobenzyl)-6-methyl-3-(methylthio)-1,2,4-triazin-5(4H)-one (17)

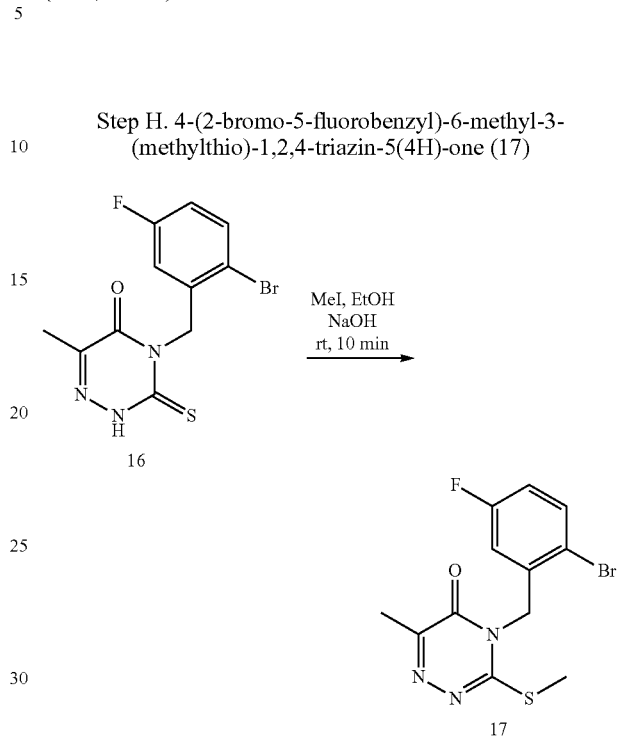

To a suspension of 4-(2-bromo-5-fluorobenzyl)-6-methyl-3-thioxo-3,4-dihydro-1,2,4-triazin-5(2H)-one (16, 914 mg, 2.77 mmol) in ethanol (15 mL) was added NaOH (111 mg, 2.77 mmol) followed by MeI (787 mg, 5.54 mmol). The mixture was stirred at RT for 10 min to produce a clear yellow solution. The reaction was diluted with water (100 mL), and extracted with EtOAc (30 mL×2). The extracts were washed with brine, dried over $MgSO_4$ and concentrated to give the crude product. This was purified by silica gel column, and eluted with 20-25% ethyl acetate in petroleum ether to give 4-(2-bromo-5-fluorobenzyl)-6-methyl-3-(methylthio)-1,2,4-triazin-5(4H)-one (17). $^1$H NMR (400 MHz, DMSO, ppm): δ 7.73 (m, 1H), 7.16 (br, 1H), 7.05 (d, 1H), 5.09 (s, 2H), 2.56 (s, 3H), 2.32 (s, 3H). MS: m/z, 344 (100%, M+1), 346 (100%).

Step I. (R)-tert-butyl 1-(4-(2-bromo-5-fluorobenzyl)-6-methyl-5-oxo-4,5-dihydro-1,2,4-triazin-3-yl)piperidin-3-ylcarbamate (18)

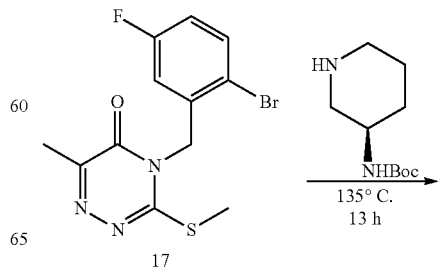

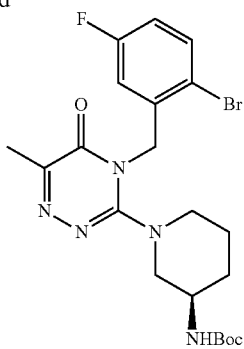

18

The mixture of 4-(2-bromo-5-fluorobenzyl)-6-methyl-3-(methylthio)-1,2,4-triazin-5(4H)-one (17, 180 mg, 0.523 mmol) and (R)-tert-butyl piperidin-3-ylcarbamate (208 mg, 1.04 mmol) was ground for 5 min and then heated in a tube under nitrogen atmosphere at 135° C. for 13 h. The mixture was separated by silica gel column, and eluted with 10-50% ethyl acetate in petroleum ether to give (R)-tert-butyl 1-(4-(2-bromo-5-fluorobenzyl)-6-methyl-5-oxo-4,5-dihydro-1,2,4-triazin-3-yl)piperidin-3-ylcarbamate (18). MS: m/z, 496 (100%, M+1), 498 (100%).

Step J. (R)-3-(3-aminopiperidin-1-yl)-4-(3-fluorobenzyl)-6-methyl-1,2,4-triazin-5(4H)-one (19)

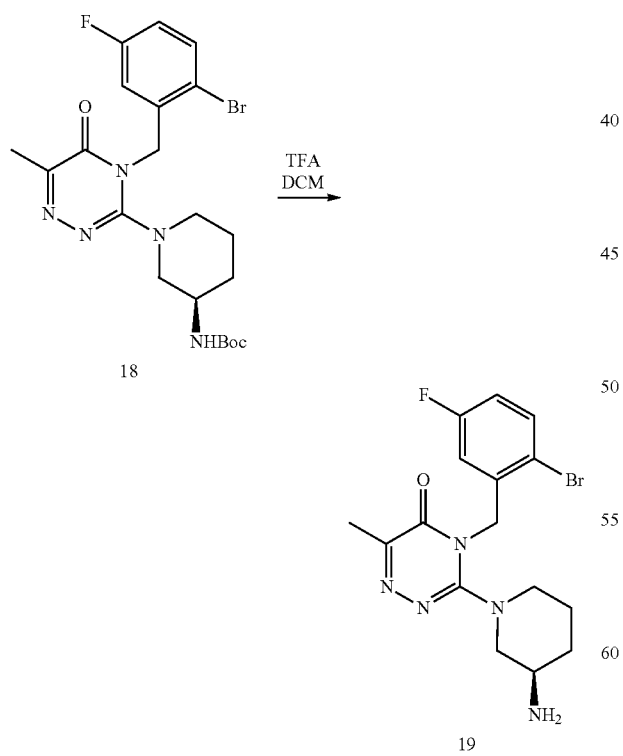

To a solution of (R)-tert-butyl 1-(4-(2-bromo-5-fluorobenzyl)-6-methyl-5-oxo-4,5-dihydro-1,2,4-triazin-3-yl)piperidin-3-ylcarbamate (18, 30 mg) in dichloromethane (1 mL) was added TFA (0.5 mL), and the mixture was stirred at RT for 3 h. The mixture was carefully neutralized with NaHCO₃ (aq, saturated), and extracted with CH₂Cl₂ (10 mL×3). The combined extracts were dried over Na₂SO₄ and concentrated to give the crude product. This was purified by column chromatography on silica gel, and eluted with 92:6:2 dichloromethane-methanol-ammonia to provide (R)-3-(3-aminopiperidin-1-yl)-4-(3-fluorobenzyl)-6-methyl-1,2,4-triazin-5(4H)-one (19). MS: m/z, 396 (100%, M+1), 398 (100%).

Example 3

(R)-2-((3-(3-aminopiperidin-1-yl)-6-methyl-5-oxo-1,2,4-triazin-4(5H)-yl)methyl)-4-fluorobenzonitrile Step A. (R)-tert-butyl 1-(4-(2-cyano-5-fluorobenzyl)-6-methyl-5-oxo-4,5-dihydro-1,2,4-triazin-3-yl)piperidin-3-ylcarbamate (20)

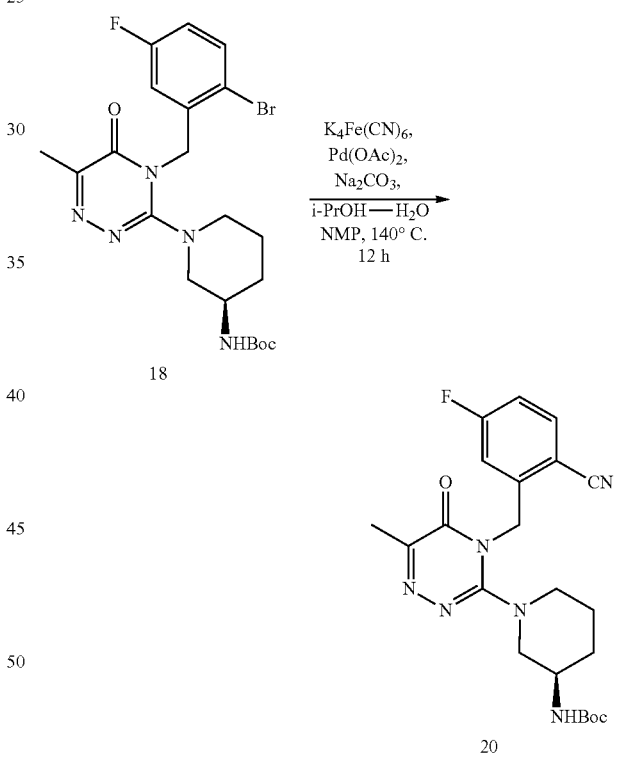

To a mixture of Na₂CO₃ (53 mg, 0.50 mmol) and Pd(OAc)₂ (3 mg, 0.013 mmol) in NMP (0.5 mL) was added i-PrOH (3 drops) and water (2 drops). The mixture was stirred at RT for 5 min. A solution of (R)-tert-butyl 1-(4-(2-bromo-5-fluorobenzyl)-6-methyl-5-oxo-4,5-dihydro-1,2,4-triazin-3-yl) piperidin-3-ylcarbamate (18, 246 mg, 0.496 mmol) in NMP (1.0 mL) was added. The mixture was heated to 140° C. and then K₄[Fe(CN)₆].3H₂O (209 mg, 0.496 mmol) was added. The mixture was heated at 140° C. for 12 h. After cooling to RT, the mixture was diluted with water (10 mL), and extracted with EtOAc (20 mL×2). The combined extracts were washed with brine, dried over MgSO₄, and concentrated to give crude product. This was purified by column chromatography on silica gel, and eluted with 20-35% EtOAc in petroleum ether to provide (R)-tert-butyl 1-(4-(2-cyano-5-fluorobenzyl)-6-methyl-5-oxo-4,5-dihydro-1,2,4-triazin-3-yl)piperidin-3-yl-carbamate (20). MS: m/z, 418 (20%), 443 (100%, M+1), 465 (95%, M+23).

Step B. (R)-2-((3-(3-aminopiperidin-1-yl)-6-methyl-5-oxo-1,2,4-triazin-4(5H)-yl)methyl)-4-fluorobenzonitrile (21)

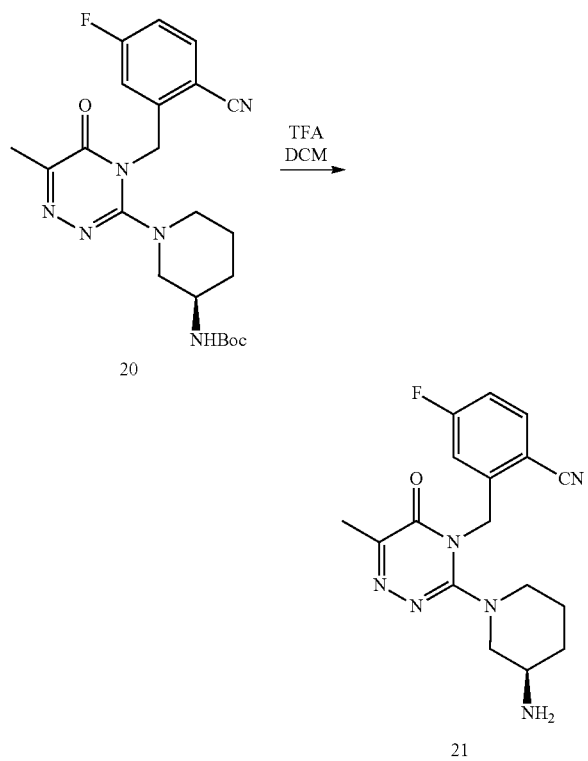

To a solution of (R)-tert-butyl 1-(4-(2-cyano-5-fluorobenzyl)-6-methyl-5-oxo-4,5-dihydro-1,2,4-triazin-3-yl)piperidin-3-ylcarbamate (20, 37 mg) in dichloromethane (1 mL) was added TFA (0.5 mL) and the mixture was stirred at RT for 1 h. The mixture was carefully neutralized with NaHCO₃ (aq, saturated), and extracted with CH₂Cl₂ (10 mL×3). The combined extracts were dried over Na₂SO₄ and concentrated to give the crude product, which was purified by column chromatography on silica gel, and eluted with 92:6:2 dichloromethane-methanol-ammonia to provide (R)-2-((3-(3-aminopiperidin-1-yl)-6-methyl-5-oxo-1,2,4-triazin-4(5H)-yl)methyl)-4-fluorobenzonitrile (21). $^1$H NMR (400 MHz, DMSO, ppm): δ 7.96 (m, 1H), 7.36 (br, 1H), 7.29 (d, 1H), 5.23 (s, 2H), 3.15 (m, 3H), 2.72 (m, 2H), 2.23 (s, 3H), 1.78 (d, 1H), 1.64 (d, 1H), 1.47 (m, 1H), 1.12 (m, 1H). MS: m/z, 343 (100%, M+1);

Example 4

(R)-3-(3-aminopiperidin-1-yl)-4-(2-chloro-5-fluorobenzyl)-6-methyl-1,2,4-triazin-5(4H)-one Step A. Methyl 2-chloro-5-fluorobenzoate (23)

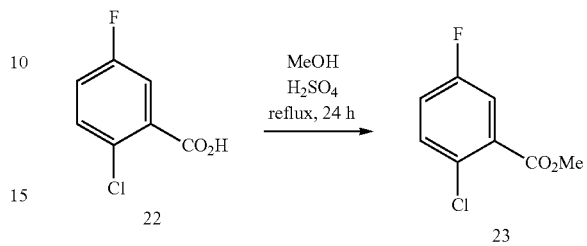

To a solution of 2-chloro-5-fluorobenzoic acid (22) (35.0 g, 200 mmol) in methanol (350 mL) was added conc. H₂SO₄ (5 mL). The mixture was heated at reflux for 24 h. Most of the solvent was evaporated, and the resulting mixture was diluted with water (300 mL). The mixture was extracted with EtOAc (150 mL×2). The combined extracts were washed with saturated NaHCO₃ and brine, dried over MgSO₄, and concentrated to give methyl 2-chloro-5-fluorobenzoate (23).

Step B. (2-chloro-5-fluorophenyl)methanol (24)

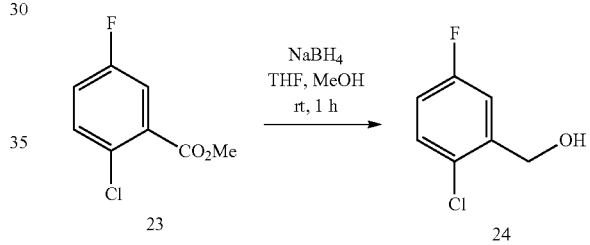

To a solution of methyl 2-chloro-5-fluorobenzoate (23, 35.0 g, 185.6 mmol) in dry THF (150 mL) was added NaBH₄ (21.2 g, 557 mmol). Methanol (40 mL) was added dropwise at RT. After the addition, the mixture was stirred at RT for 1 h. Water (300 mL) was slowly added. The mixture was extracted with CH₂Cl₂ (200 mL×2). The combined extracts were washed with saturated NaHCO₃ and brine, dried over MgSO₄, and concentrated to give (2-chloro-5-fluorophenyl)methanol (24).

Step C. 2-(bromomethyl)-1-chloro-4-fluorobenzene (25)

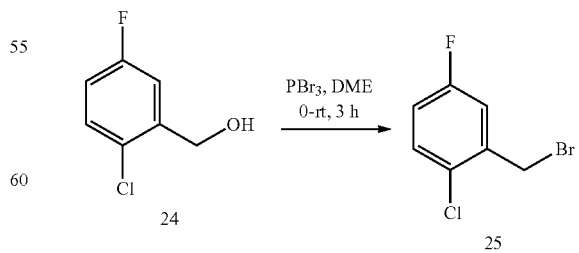

To a solution of (2-chloro-5-fluorophenyl)methanol (24, 25.5 g, 159 mmol) in dry DME (200 mL) at 0° C. was added a solution of PBr₃ (25.8 g, 95.2 mmol) in dry DME (150 mL)

dropwise. The mixture was then slowly warmed up to RT and stirred at RT for another 3 h. The mixture was diluted with water (300 mL), and extracted with 1:1 petroleum-ether-EtOAc (200 mL×2). The combined extracts were washed with saturated NaHCO₃ and brine, dried over MgSO₄, and concentrated to give 2-(bromomethyl)-1-chloro-4-fluorobenzene (25).

Step D.
1-chloro-4-fluoro-2-(isothiocyanatomethyl)benzene (26)

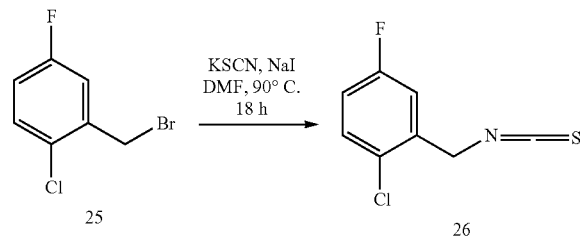 [SMILES: Fc1ccc(Cl)c(CBr)c1 ; Fc1ccc(Cl)c(CN=CC=S)c1]

To a solution of 2-(bromomethyl)-1-chloro-4-fluorobenzene (25, 22.3 g, 100 mmol) in dry DMF (150 mL) were added NaI (16.0 g, 107 mmol) and KSCN (19.5 g, 200 mmol) The mixture was heated under N₂ at 90° C. for 18 h. After cooling to RT, the mixture was diluted with water (200 mL), and extracted with EtOAc (200 mL×2). The combined extracts were washed with brine, dried over MgSO₄, and concentrated to give crude product. This was purified by column chromatography on silica gel, and eluted with petroleum ether to provide 1-chloro-4-fluoro-2-(isothiocyanatomethyl)benzene (26).

Step E.
N-(2-chloro-5-fluorobenzyl)hydrazinecarbothioamide (27)

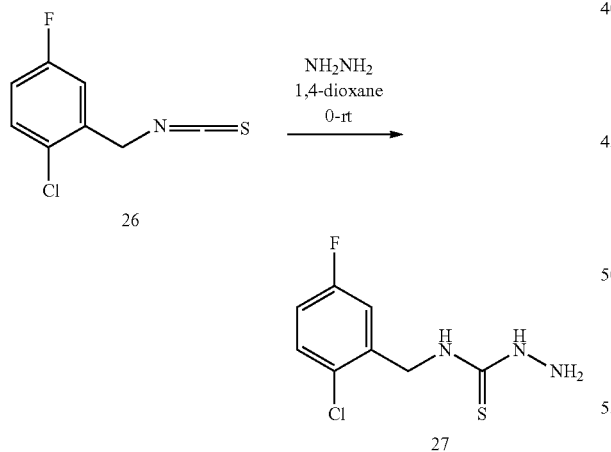

To a solution of hydrazine hydrate (80%, 13.4 g, 214 mmol) in 1,4-dioxane (100 mL) at 0° C. was added a solution of 1-chloro-4-fluoro-2-(isothiocyanatomethyl)benzene (26, 14.4 g, 71.6 mmol) in 1,4-dioxane (50 mL) The mixture was stirred at RT for 2 h. Ice cold water (300 mL) was added. The precipitated solid was collected by filtration, washed with water and dried over P₂O₅ overnight to provide N-(2-chloro-5-fluorobenzyl)hydrazinecarbothioamide (27). MS: m/z, 234 (100%, M+1), 236 (33%).

Step F. Methyl 2-(2-(2-chloro-5-fluorobenzylcarbamothioyl)hydrazono)propanoate (28)

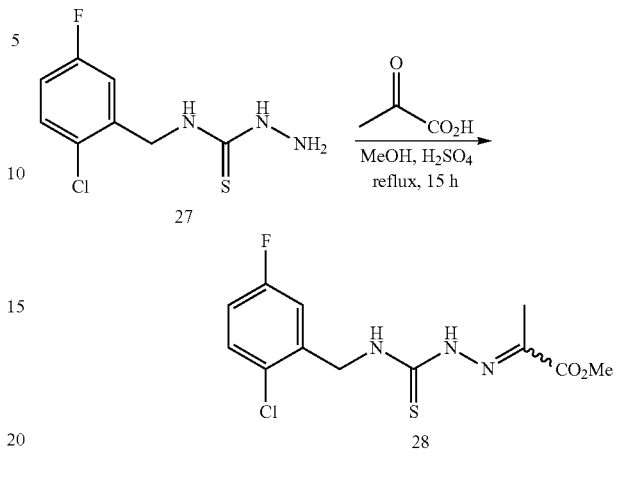

To a solution of pyruvic acid (5.63 g, 64.0 mmol) in methanol (150 mL) was added N-(2-chloro-5-fluorobenzyl)hydrazinecarbothioamide (27, 14.9 g, 64.0 mmol) followed by conc. H₂SO₄ (3 mL) The mixture was heated at reflux for 15 h. Most of the solvent was evaporated. The resulting residue was taken into EtOAc (500 mL), washed with water, saturated NaHCO₃ and brine, dried over MgSO₄, and concentrated to give methyl 2-(2-(2-chloro-5-fluorobenzylcarbamothioyl)hydrazono)propanoate (28). MS: m/z, 318 (100%, M+1), 320 (35%).

Step G. 4-(2-chloro-5-fluorobenzyl)-6-methyl-3-thioxo-3,4-dihydro-1,2,4-triazin-5(2H)-one (29)

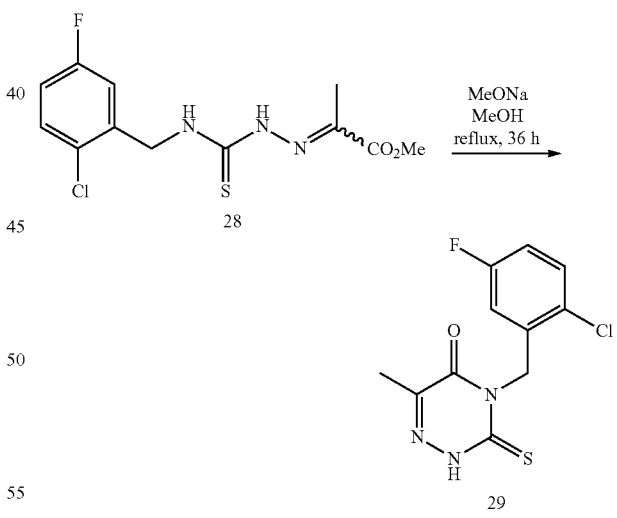

To a solution of MeONa (0.82 M) in methanol (200 mL), freshly prepared from sodium (3.80 g, 165 mmol) and dry methanol (200 mL), was added methyl 2-(2-(2-chloro-5-fluorobenzylcarbamothioyl)hydrazono)propanoate (28, 10.00 g, 31.5 mmol). The mixture was heated at reflux for 36 h. Most of the solvent was evaporated. The resulting residue was diluted with water (300 mL), acidified with 2 N HCl to pH=1~2, and then extracted with EtOAc (250 mL×2). The extracts were washed with brine, dried over MgSO₄, and concentrated to give a mixture, which was separated by silica gel column, and eluted with 20-30% ethyl acetate in petroleum ether to give 4-(2-chloro-5-fluorobenzyl)-6-methyl-3-thioxo-3,4-dihydro-1,2,4-triazin-5(2H)-one (29).

Step H. 4-(2-chloro-5-fluorobenzyl)-6-methyl-3-(methylthio)-1,2,4-triazin-5(4H)-one (30)

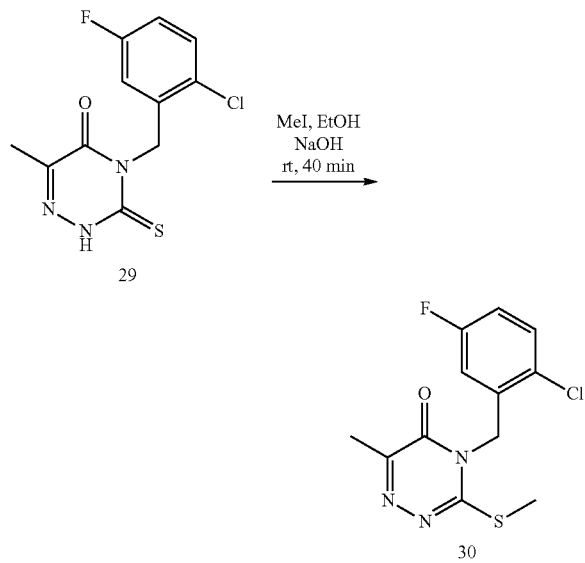

To a suspension of 4-(2-chloro-5-fluorobenzyl)-3-thioxo-3,4-dihydro-1,2,4-triazin-5(2H)-one (29, 3.06 g, 10.72 mmol) in ethanol (50 mL) was added MeI (2.44 g, 17.1 mmol) followed by NaOH (429 mg, 10.72 mmol). The mixture was stirred at RT for 40 min to produce a clear yellow solution. The reaction was diluted with water (200 mL), and extracted with EtOAc (100 mL×3). The extracts were washed with brine, dried over MgSO$_4$, and concentrated to give the crude product (3.195 g). This was crystallized from ethyl acetate-petroleum ether to give 4-(2-chloro-5-fluorobenzyl)-6-methyl-3-(methylthio)-1,2,4-triazin-5(4H)-one (30). MS: m/z, 300 (100%, M+1), 302 (35%).

Step I. (R)-tert-butyl 1-(4-(2-chloro-5-fluorobenzyl)-6-methyl-5-oxo-4,5-dihydro-1,2,4-triazin-3-yl)piperidin-3-ylcarbamate (31)

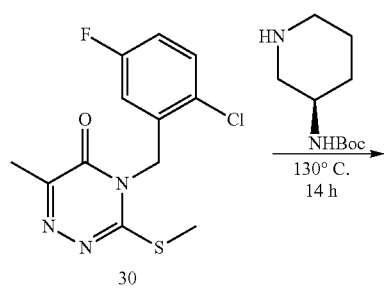

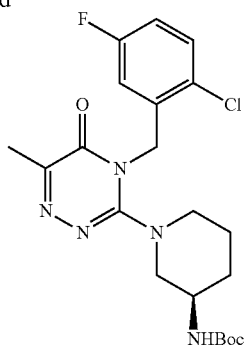

The mixture of 4-(2-chloro-5-fluorobenzyl)-6-methyl-3-(methylthio)-1,2,4-triazin-5(4H)-one (30, 1.50 g, 5.0 mmol) and (R)-tert-butyl piperidin-3-ylcarbamate (1.500 g, 7.50 mmol) was ground for 5 min and then heated in a tube under nitrogen atmosphere at 130° C. for 14 h. The mixture was separated by silica gel column, and eluted with 10-50% ethyl acetate in petroleum ether to give (R)-tert-butyl 1-(4-(2-chloro-5-fluorobenzyl)-6-methyl-5-oxo-4,5-dihydro-1,2,4-triazin-3-yl)piperidin-3-ylcarbamate (31). MS: m/z, 396 (100%, M-56), 398 (35%), 452 (100%, M+1), 454 (35%), 474 (70%, M+23), 476 (25%).

Step J. (R)-3-(3-aminopiperidin-1-yl)-4-(2-chloro-5-fluorobenzyl)-6-methyl-1,2,4-triazin-5(4H)-one (32)

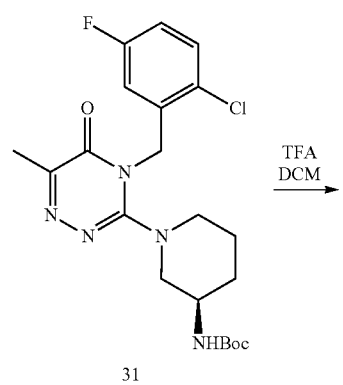

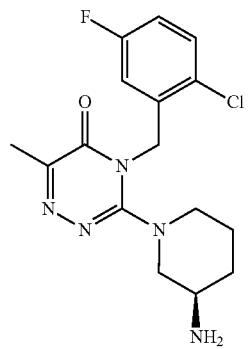

To a solution of (R)-tert-butyl 1-(4-(2-chloro-5-fluorobenzyl)-6-methyl-5-oxo-4,5-dihydro-1,2,4-triazin-3-yl)piperidin-3-ylcarbamate (31, 44 mg) in dichloromethane (1 mL)

was added TFA (0.4 mL), and the mixture was stirred at RT for 1.5 h. The mixture was carefully neutralized with NaHCO$_3$ (aq, saturated), and extracted with CH$_2$Cl$_2$ (10 mL×3). The combined extracts were dried over Na$_2$SO$_4$ and concentrated to give (R)-3-(3-aminopiperidin-1-yl)-4-(2-chloro-5-fluorobenzyl)-6-methyl-1,2,4-triazin-5(4H)-one (32). MS: m/z, 352 (100%, M+1), 354 (33%).

DPP-4 Activity In Vitro

DPP-IV Assay Solutions of test compounds in varying concentrations (10$^{-5}$ mol/L, 10$^{-6}$ mol/L, 10$^{-7}$ mol/L, 10$^{-8}$ mol/L, 10$^{-9}$ mol/L, 10$^{-10}$ mol/L, 10$^{-11}$ mol/L, and 10$^{-12}$ mol/L) were prepared in dimethyl sulfoxide (DMSO) and then diluted into assay buffer comprising: 10 mM Tris-HCl pH 8.0, 0.2 M NaCl, and 0.1% BSA. Recombinant human DPP-IV (7.8 ng/ml final concentration) was added to the dilutions and pre-incubated for 30 mins at room temperature before the reaction was initiated with H-Ala-Pro-AFC (50 µM final concentration). The total volume of the reaction mixture was 100 µl.

The fluorescence of the mixture was measured after 30 minutes (excitation at 405 nm; emission at 535 nm). Inhibition constants (IC$_{50}$) were calculated by GraphPad Prism.

The test results are listed in Table 1.

TABLE 1

| EXAMPLE | IC$_{50}$ (nM) |
|---|---|
| 1 | 22 |
| 2 | 242 |
| 3 | 3 |
| 4 | 640 |

DPP-4 Activity In Vivo

Compounds were tested in mice to assess inhibition of plasma DPP-4 activity. Male ICR mice (25-30 g) were used for this study. All the mice were fasted at least 3 hours before study. Mice (n=6/group) received vehicle or compound by oral gavages. The dosing solutions were 0.15 mg/ml for the 3 mg/kg. Dosing volumes were 20 ml/kg of body weight for all doses. The vehicle was distilled water. Following oral administration, blood samples were obtained manually at designed schedule. Blood samples were processed to obtain plasma (2000 G, 5 min, 4° C.) within 15 min after sampling.

Plasma were collected and tested by fluorometry. Before the testing, 80 mM MgCl$_2$ buffer was added into the 5 ul serum samples and pre-incubated for 5 minutes at RT, then 10 µl of 0.1 mM substrate Gly-Pro-AMC and 20 µl buffer were added into them. The fluorescence of the mixture was measured every 3 minutes after mixing (excitation at 380 nm; emission at 460 nm). The DPP-4 activity before administration was 100%. The relative activity of DPP-4 in serum was calculated using the formula below:

Relative DPP-4 activity %=DPP-4 activity after dosing/DPP-4 activity before dosing×100.

The relative DPP-4 activities in mice plasma after oral administration of a 3 mg/kg dose of Example 3 to ICR mice are listed in Table 2 below:

TABLE 2

| | | Relative DPP-4 activity at the dosage of 3 mg/kg (DPP-4 Relative activity %, $\overline{X} \pm s$, n = 5) | | | | |
|---|---|---|---|---|---|---|
| | Dosage | | Time after dosing (hour) | | | |
| Group | (mg/kg) | 0 | 1 hr | 2 hrs | 3 hrs | 5 hrs |
| control | — | 100.0 | 91.8 ± 3.3 | 90.3 ± 4.8 | 88.9 ± 2.5 | 93.6 ± 5.3 |
| Alogliptin | 3 | 100.0 | 18.8 ± 1.0*** | 19.9 ± 1.3*** | 22.3 ± 1.5*** | 25.6 ± 1.6*** |
| Example 3 | 3 | 100.0 | 14.1 ± 2.0*** | 16.7 ± 1.6*** | 19.8 ± 1.0*** | 18.7 ± 1.8*** |

*P < 0.05;

**P < 0.01;

***P < 0.001; Relative to control group

What is claimed is:

1. A compound of formula (I):

(I)

or a pharmaceutically acceptable salt thereof, wherein
R$^1$ is selected from:
  C$_{1-10}$ alkyl,
  C$_{3-10}$ cycloalkyl,
  C$_{3-10}$ cycloalkylalkyl,
  heterocyclyl,
  heterocyclylalkyl,
  aryl,
  arylalkyl,
  heteroaryl, and
  heteroarylalkyl,
  wherein alkyl, cycloalkyl, and heterocyclyl are each unsubstituted or substituted with at least one substituent independently selected from R$^{6a}$, and wherein aryl and heteroaryl are each unsubstituted or independently substituted with at least one substituent independently selected from R$^{6b}$;
R$^2$ is alkyl,
  wherein each alkyl is unsubstituted or substituted with at least one substituent independently selected from R$^{6a}$;

$R^3$ is selected from:
  hydrogen,
  halogen,
  hydroxyl,
  $C_{1-4}$ alkyl,
  $C_{2-4}$ alkenyl,
  $C_{2-4}$ alkynyl,
  $C_{3-7}$ cycloalkyl,
  heterocyclyl,
  $C_{3-7}$ cycloalkylalkyl,
  heterocyclylalkyl,
  aryl,
  heteroaryl,
  arylalkyl, and
  heteroarylalkyl,
  wherein alkyl, alkenyl, alkynyl, cycloalkyl, and heterocyclyl are each unsubstituted or substituted with at least one substituent independently selected from $R^{6a}$, and aryl and heteroaryl are each unsubstituted or substituted with at least one substituent independently selected from $R^{6b}$;

$R^4$ is selected from:
  hydrogen, and
  $C_{1-4}$ alkyl,
  wherein alkyl is unsubstituted or substituted with at least one substituent independently selected from $R^{6a}$;

$R^5$ is selected from:
  hydrogen, and
  $C_{1-4}$ alkyl,
  wherein alkyl is unsubstituted or substituted with at least one substituent independently selected from $R^{6a}$;

or $R^4$ and $R^5$ together with the nitrogen to which they are attached form a heterocyclic ring;

each $R^{6a}$ is independently selected from:
  —$OR^8$,
  —$NR^7S(O)_mR^8$,
  —$NO_2$,
  halogen,
  —$S(O)_mR^7$,
  —$SR^8$,
  —$S(O)_2OR^7$,
  —$OS(O)_2R^8$,
  —$S(O)_mNR^7R^8$,
  —$NR^7R^8$,
  —$O(CR^9R^{10})_nNR^7R^8$,
  —$C(O)R^7$,
  —$CO_2R^8$,
  —$CO_2(CR^9R^{10})_nCONR^7R^8$,
  —$OC(O)R^7$,
  —CN,
  —$C(O)NR^7R^8$,
  —$NR^7C(O)R^8$,
  —$OC(O)NR^7R^8$,
  —$NR^7C(O)OR^8$,
  —$NR^7C(O)N^7OR^8$,
  —$CR^7(N—OR^8)$,
  —$CF_2$,
  —$CF_3$,
  —$OCF_2$, and
  —$OCF_3$;

each $R^{6b}$ is independently selected from:
  $R^{6a}$,
  $C_{1-10}$ alkyl,
  aryl,
  aryl-$C_{1-4}$ alkyl,
  heteroaryl, and
  heteroaryl-$C_{1-4}$ alkyl;

$R^7$ and $R^8$ are independently selected from:
  hydrogen,
  $C_{1-10}$ alkyl,
  $C_{2-10}$ alkenyl,
  $C_{2-10}$ alkynyl,
  cycloalkyl,
  cycloalkyl-$C_{1-10}$ alkyl;
  heterocyclyl,
  heterocyclyl-$C_{1-10}$ alkyl,
  aryl,
  heteroaryl,
  aryl-$C_{1-10}$ alkyl, and
  heteroaryl-$C_{1-10}$ alkyl,
  wherein alkyl, alkenyl, alkynyl, cycloalkyl, and heterocyclyl are each unsubstituted or substituted with at least one substituent independently selected from $R^{6a}$, and aryl and heteroaryl are each unsubstituted or substituted with at least one substituent independently selected from $R^{6b}$; or $R^7$ and $R^8$ together with the atom(s) to which they are attached form a heterocyclic ring of 4 to 7 members containing 0, 1, or 2 additional heteroatoms independently selected from oxygen, sulfur and $NR^{11}$, each $R^7$ and $R^8$ may be unsubstituted or substituted on a carbon or nitrogen atom with at least one substituent selected from $R^{12}$;

$R^9$ and $R^{10}$ are independently selected from hydrogen, $C_{1-10}$ alkyl, $C_{2-10}$ alkenyl, $C_{2-10}$ alkynyl, cycloalkyl, cycloalkyl-$C_{1-10}$ alkyl, heterocyclyl, heterocyclyl —$C_{1-10}$ alkyl, aryl, heteroaryl, aryl-$C_{1-10}$ alkyl, and heteroaryl-$C_{1-10}$ alkyl; or $R^9$ and $R^{10}$ together with the carbon to which they are attached form a ring of 3 to 7 members containing 0, 1, or 2 heteroatoms independently selected from oxygen, sulfur and nitrogen;

each $R^{11}$ is independently selected from:
  hydrogen,
  $C_{1-10}$ alkyl,
  $C_{3-8}$ cycloalkyl,
  $C_{3-8}$ cycloalkyl-$C_{1-4}$ alkyl,
  heterocyclyl,
  heterocyclyl-$C_{1-4}$ alkyl,
  aryl,
  aryl-$C_{1-4}$ alkyl,
  heteroaryl,
  heteroaryl-$C_{1-4}$ alkyl,
  —$S(O)_mR^7$,
  —$C(O)R^7$,
  —$CO_2R^7$,
  —$CO_2(CR^9R^{10})_nCONR^7R^8$, and
  —$C(O)NR^7R^8$;

each $R^{12}$ is independently selected from:
  halogen,
  $C_{1-10}$ alkyl,
  $C_{3-8}$ cycloalkyl,
  $C_{3-8}$ cycloalkylalkyl,
  heterocyclyl,
  heterocyclyalkyl,
  aryl,
  aryl-$C_{1-4}$ alkyl,
  heteroaryl,
  heteroaryl-$C_{1-4}$ alkyl,
  —$OR^7$,
  —$NR^7S(O)_mR^8$,
  —$S(O)_mR^7$,
  —$SR^7$,
  —$S(O)_2OR^7$, —OS(O)$_2$R$^7$,
—S(O)$_m$NR$^7$R$^8$,
—NR$^7$R$^8$,
—O(CR$^9$R$^{10}$)$_n$NR$^7$R$^8$,
—C(O)R$^7$,
—CO$_2$R$^8$,
—CO$_2$(CR$^9$R$^{10}$)$_n$CONR$^7$R$^8$,
—OC(O)R$^7$,
—CN,
—C(O)NR$^7$R$^8$,
—NR$^7$C(O)R$^8$,
—OC(O)NR$^7$R$^8$,
—NR$^7$C(O)OR$^8$,
—NR$^7$C(O)NR$^7$R$^8$,
—CF$_2$,
—CF$_3$,
—OCF$_2$, and
—OC$_3$;

L is —CR$^7$R$^8$—;

m is selected from 1 and 2; and n is selected from 1, 2, and 3.

2. The compound of claim 1, or a pharmaceutically acceptable salt thereof, wherein L is —CR$^7$R$^8$, and at least one of R$^7$ and R$^8$ is hydrogen.

3. The compound of claim 1, or a pharmaceutically acceptable salt thereof, wherein L is —CH$_2$.

4. The compound of claim 1, or a pharmaceutically acceptable salt thereof, wherein R$^2$ is methyl.

5. The compound of claim 1, and/or at least one pharmaceutically acceptable salt thereof, wherein R$^1$ is aryl optionally substituted with at least one substituent independently selected from R$^{6b}$.

6. The compound of claim 5, or a pharmaceutically acceptable salt thereof, wherein R$^1$ phenyl optionally substituted with at least one substituent independently selected from R$^{6b}$.

7. The compound of claim 6, or a pharmaceutically acceptable salt thereof, wherein R$^1$ is phenyl, optionally substituted with at least one substituent selected from halogen and cyano.

8. The compound of claim 7, or a pharmaceutically acceptable salt thereof, wherein R$^1$ is selected from 2-cyanophenyl, 2-chloro-5-fluorophenyl, 2-cyano-5-fluorophenyl, and 2-bromo-5-fluorophenyl.

9. The compound of claim 1, or a pharmaceutically acceptable salt thereof, wherein R$^3$ is hydrogen.

10. The compound of claim 1, or a pharmaceutically acceptable salt thereof, wherein R$^4$ is hydrogen.

11. The compound of claim 1, or a pharmaceutically acceptable salt thereof, wherein R$^5$ is hydrogen.

12. A pharmaceutical composition which comprises a compound of claim 1, or a pharmaceutically acceptable salt thereof, and at least one pharmaceutically acceptable carrier.

13. A method of treating a condition responsive to inhibition of dipeptidyl peptidase-IV enzyme comprising administering to a patient in recognized need thereof an effective amount of a compound of claim 1, or a pharmaceutically acceptable salt thereof.

14. A method for treating a condition selected from insulin resistance, hyperglycemia, and type II diabetes comprising administering to a patient in recognized need thereof an effective amount of a compound of claim 1, or a pharmaceutically acceptable salt thereof.

* * * * *